United States Patent
Kawakita et al.

(10) Patent No.: US 6,839,642 B2
(45) Date of Patent: Jan. 4, 2005

(54) FLEXURE LIFE ESTIMATING METHOD, WIRE HARNESS DESIGNING METHOD AND PROGRAM THEREOF

(75) Inventors: Yuki Kawakita, Mie (JP); Takuya Inoue, Mie (JP); Hitoshi Kawabe, Mie (JP); Hisayoshi Onoue, Mie (JP); Masaru Furusyo, Osaka (JP); Kouji Ohuchi, Osaka (JP); Mikio Kaji, Osaka (JP)

(73) Assignees: Sumitomo Wiring Systems, Ltd., Yokkaichi (JP); Sumitomo Electric Industries, Ltd., Osaka (JP)

( * ) Notice: Subject to any disclaimer, the term of this patent is extended or adjusted under 35 U.S.C. 154(b) by 140 days.

(21) Appl. No.: 10/084,947

(22) Filed: Mar. 1, 2002

(65) Prior Publication Data

US 2002/0161535 A1 Oct. 31, 2002

(30) Foreign Application Priority Data

Mar. 2, 2001 (JP) .................................. 2001-057945
Mar. 2, 2001 (JP) .................................. 2001-058445
Nov. 7, 2001 (JP) .................................. 2001-341614

(51) Int. Cl.$^7$ ............................................. G02N 3/32
(52) U.S. Cl. ............................. 702/42; 702/34; 73/812
(58) Field of Search ............................. 702/181, 183, 702/34, 35, 42; 73/812; 703/2, 7

(56) References Cited

U.S. PATENT DOCUMENTS 6,163,757 A * 12/2000 Aizawa et al. ................. 702/42
6,272,387 B1 * 8/2001 Yoon ............................. 700/83

FOREIGN PATENT DOCUMENTS

JP 08166333 6/1996
WO 01/08172 2/2001

OTHER PUBLICATIONS

CableCad; Mar. 17, 1999, www.cablecad.com.*

* cited by examiner

*Primary Examiner*—Marc S. Hoff
*Assistant Examiner*—Paul L Kim
(74) *Attorney, Agent, or Firm*—Greenblum & Bernstein, P.L.C.

(57) ABSTRACT

Diameters and the number of respective wires are inputted, and a diameter of a virtual wire formed by converting a wire bundle to a model through a predetermined arithmetic expression derived from rule of thumb, and based upon this, a flexure life estimating process of the virtual wire is carried out. It is possible to easily estimate the flexure life and also to estimate the flexure life and obtain the results immediately after an application subject and a wire harness to be placed have been designed; thus, it becomes possible to shorten the developing period.

16 Claims, 24 Drawing Sheets

FLEXURE LIFE ESTIMATING METHOD, WIRE HARNESS DESIGNING METHOD AND PROGRAM THEREOF

BACKGROUND OF THE INVENTION

1. Field of the Invention

The present invention relates to a wire harness designing method for designing a wire harness that is placed on a desired application subject and also to techniques related thereto, and more particularly concerns a wire harness flexure life estimating method and techniques related thereto which estimate the flexure life of a wire bundle up to disconnection due to repeated bending processes, the wire bundle being formed by binding wires, each having a conductor line coated with an insulating layer, and used for supplying electric signals and power from a power supply of a car, an industrial apparatus and an electric or electronic apparatus attached thereto.

2. Description of the Background Art

As conventionally known, many wires or wire bundles, each formed by binding a plurality of wires (in this specification, wires and wire bundles are generally referred to as "wire harnesses"), are used in cars and industrial apparatuses. Some of wire harnesses are placed at a position, such as a door portion and a seat portion, that is subjected to bending, and such wire harnesses tend to have disconnection after having received repeated bending deformations; therefore, the wire harness needs to be designed by taking its flexure life into consideration.

Conventionally, for example, wire harnesses of cars have been designed and examined while taking formation, etc. of cars into consideration on a car manufacturer side (hereinafter, referred to as "manufacturing station"), and these have been subjected to performance evaluation by using prototypes, and then manufactured.

In this case, it is difficult to completely take the flexure performance of a wire harness into consideration from the initial designing stage. Therefore, in the conventional method, after the stage in which the initial designing has been made, a prototype is formed, and in the event of any problem in evaluation tests on this prototype, designing revisions are carried out and the product is developed.

More specifically, FIG. 29 shows a designing sequence of a conventional wire harness.

First, as step T1, a designing plan is formed with respect to a vehicle body as a whole.

At the next step T2, a designing plan is formed with respect to the wire harness (indicated by "W/H" in FIG. 29) so as to match the vehicle body.

Then, at step T3, based upon the wire harness design thus planned at step T2, the wire harness is formed on a trial basis.

Successively, at step T4, the prototype wire harness is actually bent repeatedly so as to carry out flexure evaluation tests. Then, the results of the flexure evaluation tests are examined (step T5), and in the case when required flexure endurance is not obtained, a prototype is again formed at step T3, and the flexure evaluation tests (step T4) and the examinations of the results (step T5) are repeatedly carried out until the required flexure endurance has been obtained; thus, at the time when positive examination results have been finally obtained, the corresponding mass production is started (step T6).

In recent years, there have been strong demands for shortened developing periods and elimination of prototypes in the entire automobile field, and there also have been demands for improvements in the sequence of conventional jobs for manufacturing prototypes (step T3) and for executing flexure evaluation tests (steps T4, T5).

Moreover, in general, wire bundles, which are bridged over a door and the body of a car, are allowed to pass through a protective grommet used for the purpose of waterproof and prevention of scratches, and in this state, the grommet is secured to a hinge portion between the door and the body of the car. In this case, every time the door is opened and closed, the wire bundle is repeatedly extended and bent; therefore, it is important to estimate the flexure life of the wire bundle at this portion, in an attempt to manufacture a wire bundle and to select the product in the case of an attaching process.

Here, it is proposed that in order to estimate what degree of flexure life the wire bundle inside the grommet bridged over the door and the hinge portion has, a finite element method (matrix stress analyzing method) is adopted.

This finite element method is one of simulation techniques which analyze a stress distribution, etc. of a continuous body of a complex structural member by using a computer, and in this method, a structural member serving as an analysis subject is divided into finite number of elements by using triangular or rectangular finite element meshes, and a basic differential equation is set in each element, while a greater simultaneous linear equation (matrix equation) is solved so as to allow solutions of the respective elements to have continuity with solutions of the adjacent elements.

In this finite element method which divides the structural member into finite number of elements by using the finite element meshes and carries out analyses thereon as described above, in the case when the wire bundle is allowed to pass through the inside of the grommet as described above, since the grommet has a complex structure such as a bellow shape, considerably complex data need to be calculated and processed when the grommet is divided into a plurality of elements and subjected to a modeling process so as to apply the respective physical properties to each element. Moreover, the subject for estimation of the flexure life is a wire bundle that is a collection of a plurality of wire bundles; therefore, when each of the wire bundles is divided into individual elements, and subjected to a modeling process so as to estimate the flexure life of each element, a great amount of calculation processes are required.

As described above, when a wire bundle in a grommet is analyzed by using the finite element method, the load of calculation processes imposed on a computer becomes extremely high, resulting in a disadvantage of a long period of time required for calculations.

Moreover, the process for dividing the individual structural members such as the grommet and the respective wires of the wire bundle by using finite element meshes forms an extremely time-consuming process.

In general, at low temperatures including cold temperatures, an insulating layer (coating material) such as PVC becomes susceptible to cracks (coat cracks) due to fatigue fracture caused by repeated bending processes on the insulating layer. Consequently, since the conductor section (core line) at the portion having the crack is more susceptible to a local stress, disconnection at low temperatures is mainly controlled by the fatigue fracture in the insulating layer coating the conductor section.

Therefore, the applicant of the present invention has already proposed a method of estimating the flexure life of a wire (for example, in Japanese Patent Application No. 11-210650: hereinafter, referred to as "proposed example") in which, with respect to cracks on the insulating layer of a wire harness at low temperatures, a master curve indicating the correlation between the amount of change in strain and the flexure life at the corresponding insulating layer portion is preliminarily obtained and the flexure life of a wire is estimated by using this master curve.

However, the above-mentioned proposed example is a method for finding the flexure life, under states where disconnection is mainly caused by cracks on an insulating layer, and the flexure life is found based upon the number of bending processes of the insulating layer up to disconnection; therefore, it is difficult for this method to estimate the flexure life under states where disconnection occurs in the conductor section (core line) with no cracks being generated on the insulating layer. For example, at normal temperature, in some cases, the conductor section might have a disconnection prior to the occurrence of a crack on the insulating layer. Moreover, in the case when a halogen-free resin material, or PE, etc., is used as an insulating layer, even at low temperatures, the conductor section might have a disconnection prior to the occurrence of a crack on the insulating layer. However, the proposed example fails to effectively estimate the flexure life in the case when the inner conductor section has a disconnection prior to the occurrence of a crack on the insulating layer at low temperatures.

SUMMARY OF THE INVENTION

According to a first aspect of the present invention, a method of estimating flexure life of a wire harness in which, in the case when a wire bundle, formed by binding a plurality of wires each formed by coating a conductor line with an insulating layer, is allowed to pass through a predetermined protective tube and secured to an external structural member different from the protective tube, the flexure life up to disconnection due to extending and bending processes of the wire bundle caused by operations of the external structural member is estimated in accordance with a finite element method, is provided with: an initial shape determining step of: using an initial shape of a center line of the wire bundle as a substitute for an initial shape of the wire bundle so as to be determined, using an initial shape of a virtual pipe having only a margin dimension of a margin space of the protective tube with respect to the wire bundle as an inner diameter as a substitute for an initial shape of the protective tube so as to be determined, determining an initial shape of a center line of the wire bundle so that the center line of the wire bundle is not limited by two end portions of the virtual pipe, and determining an initial shape of the external structural member; an extending and bending operation analyzing step of: analyzing extending and bending shapes of the wire bundle and the protective tube by virtually estimating operations of the external structural member so as to calculate a change in curvature of the wire bundle; a calculation step of an amount of change in strain for calculating an amount of change in strain of the wire bundle that is a subject for estimation based upon the change in curvature obtained through the extending and bending operation analyzing step; and a collation step of making a collation on a life estimation curve that is preliminarily set based upon the amount of change in strain calculated in the calculation step of an amount of change in strain so as to predict the flexure life of the wire bundle.

In accordance with this aspect, when a stress of a wire bundle formed by binding a plurality of wires is stress-analyzed based upon the finite element method, it is a rule that, originally, three dimensional analyses are carried out by using individual wires as discrete infinite elements; however, in the present preferred embodiment, the individual wires are not modeled three-dimensionally as discrete structural components, but simplified them into a virtual pseudo-single wire so as to determine the entire shape; therefore, in order to calculate the initial shape and the final shape, by carrying out modeling and calculations not based upon physical properties derived from the actual construction of wire bundle, but based upon the corresponding diameter and bending elasticity of virtual single wire, it becomes possible to greatly simplify the physical properties of wire bundle and also to calculate the resulting values. Consequently, it is possible to obtain an estimated value of flexure life that is closely approximated to the actual flexure life. Therefore, upon calculating an estimated value of flexure life through finite element method (matrix stress analyzing method) by using a computer, it becomes possible to reduce the load imposed on the computer, and also to quickly converge the estimated value.

Moreover, upon determining the respective initial shapes of the wire bundle, the protective tube and the external structural member, first, the initial shape of the center line of the wire bundle is used as a substitute for the initial shape of the wire bundle, and the initial shape of a virtual pipe having only a margin dimension of a margin space of the protective tube with respect to the wire bundle as an inner diameter is used as a substitute for the initial shape of the protective tube; thus, since the initial shape of the center line of the wire bundle is determined so that the center line of the wire bundle is not limited by two end portions of the virtual pipe, it is possible to direct a curvature change reflecting the actual shape of the wire bundle and consequently to improve the estimation precision of the flexure life, in comparison with a case in which the shape of the wire bundle is limited so that the center line of the wire bundle is allowed to pass through, for example, the center point of each of the two end portions of the virtual pipe.

In this aspect, preferably, in the extending and bending operation analyzing step, a change in curvature of a center line of the wire bundle is used as a substitute for the change in curvature of the wire bundle.

More preferably, the life estimation curve represents correlation between the amount of change in strain and the number of bending processes with respect to a single wire that is obtained by actually measuring the number of bending processes up to disconnection by repeatedly bending the single wire with respect to a plurality of amounts of change in strain; and in the calculation step of an amount of change in strain, a virtual line member, formed by subjecting the respective bending modulus of elasticity of the conductor line and the insulating layer to weighting processes and averaging processes by using ratios of cross-sectional areas, is assumed, and on the assumption that the virtual line member serves as one of the wires, supposing that the bending radius is $R_1$ in any one of the wires in the furthest bent state at the position that is subjected to the greatest change in bending within an area in which the virtual line member is subjected to bending, that the bending radius is $R_2$ in the single wire in the furthest extended state, and that the radius of any one of wires that has the greatest difference between the value $R_1$ and the value $R_2$ is r, the amount of change in strain ($\Delta\epsilon$) is calculated by the following equation:

$$\Delta\epsilon = r \cdot (1/R_1 - 1/R_2)$$

With this arrangement, a single wire is subjected to bending processes and the correlation between the amount of change in strain and the actual measured values is preliminarily obtained, and with respect to the wire having the greatest amount of change in strain in the wire bundle serving as a subject for estimation or a virtual single wire formed by converting the wire bundle into a single wire model, the amount of change in strain is calculated by the finite element method, and the calculated amount of change in strain of the wire bundle to be estimated is collated with the above-mentioned correlation so that the flexure life of the wire bundle serving as a subject for estimation is estimated; therefore, independent of product conditions of the wire bundle, it becomes possible to accurately estimate the flexure life.

According to a second aspect of the present invention, the method of estimating flexure life of a wire harness, which includes a wire having at least a center conductor line in the center thereof with strands twisted on the periphery of the center conductor line, and has a function for estimating flexure life up to disconnection of the wire due to bending and extending processes, is provided with the steps of: preliminarily obtaining a correlation between an amount of change in strain of a single wire that is made of the same material as the center conductor line and actual measured values of flexure life; calculating the greatest amount of change in strain of the center conductor line of a wire serving as a subject for the estimation; and estimating flexure life of the wire by collating the calculated greatest amount of change in strain of the center conductor line with the correlation.

According to a third aspect of the present invention, the method of estimating flexure life of a wire harness, which includes a wire bundle formed by binding a plurality of wires, each having a central conductor line in the center thereof, and has a function for estimating flexure life up to disconnection of the wire bundle, is provided with the steps of: preliminarily obtaining a correlation between an amount of change in strain of a single wire that is made of the same material as the center conductor line and actual measured values of flexure life; calculating the greatest amount of change in strain of the center conductor line of a single wire that is assumed to have the greatest change in curvature radius upon being bent among the wires within the wire bundle serving as a subject for the estimation; and estimating flexure life of the wire bundle by collating the calculated greatest amount of change in strain of the center conductor line of the wire with the correlation.

In the second aspect or the third aspect, preferably, in the step of obtaining the correlation, the single wire is repeatedly bent with respect to a plurality of amounts of change in strain to actually measure the number of bending processes up to disconnection so as to obtain the above-mentioned correlation.

More preferably, in the calculation step of the greatest amount of change in strain, supposing that the center conductor line has a radius of r, that the bending radius is $R_1$ in the center conductor line in the furthest bent state at the position that is subjected to the greatest change in bending within an area in which the center conductor line is subjected to bending, and that the be radius is $R_2$ in the center conductor line in the furthest extended state, the greatest amount of change in strain ($\Delta\epsilon$) is calculated by the following equation:

$$\Delta\epsilon = r \cdot (1/R - 1/R_2)$$

In accordance with the second aspect or the third aspect, upon estimating the flexure life of a wire or a wire bundle having at least a center conductor line in the center up to disconnection due to bending applied thereto, first, the correlation between an amount of change in strain of a single wire and actual measured values of flexure life is preliminarily obtained, and the greatest amount of change in strain is collated with the correlation so that flexure life of the wire or the wire bundle is estimated. Therefore, in particular, in the case when the conductor section serving as a core line is susceptible to disconnection prior to cracks occurring in an insulating layer serving as a coating material, it is possible to easily estimate the flexure life.

In this case, in either of a wire having a plurality of core lines and a wire bundle, only the flexure life of any one of the center conductor lines is estimated without the necessity of estimating the flexure life of all the core lines; therefore, in the case when the flexure life is estimated in a computer analyzing process, etc., by using a finite element method, it becomes possible to greatly reduce the computer calculation processing load such as setting of the finite element model and calculations of the greatest amount of change in strain.

According to a fourth aspect of the present invention, a wire harness designing method of the present invention, which is used for designing a wire harness in which a single or a plurality of wires, each formed by coating a conductor line with an insulating layer, are bound and placed on a desired application subject, is provided with: an application subject design planning step of planning a design of the application subject as a whole; a wire harness design planning step of planning a design of the wire harness so as to fit to the application subject; and a flexure life estimating step of, in the case when the wire harness planned in the wire harness design planning step is allowed to pass through a predetermined protective tube and secured to an external structural member different from the protective tube, estimating flexure life up to disconnection caused by extending and bending processes of the wire harness in accordance with a finite element method, and in this arrangement, the flexure life estimating step is provided with: an initial shape determining step of: using an initial shape of a center line of the wire harness as a substitute for an initial shape of the wire harness so as to be determined, using an initial shape of a virtual pipe having only a margin dimension of a margin space of the protective tube with respect to the wire harness as an inner diameter as a substitute for an initial shape of the protective tube so as to be determined, determining an initial shape of a center line of the wire harness so that the center line of the wire harness is not limited by two end portions of the virtual pipe, and determining an initial shape of the external structural member; an extending and bending operation analyzing step of: analyzing extending and bending shapes of the wire harness and the protective tube by virtually estimating operations of the external structural member so as to calculate a change in curvature of the wire harness; a calculation step of an amount of change in strain for calculating an amount of change in strain of the wire harness that is a subject for estimation based upon the change in curvature obtained through the extending and bending operation analyzing step; and a collation step of: making a collation on a life estimation curve that is preliminarily set based upon the amount of change in strain calculated in the calculation step of an amount of change in strain so as to predict the flexure life of the wire harness.

According to a fifth aspect of the present invention, a wire harness designing method, which is used for designing a wire harness in which a single or a plurality of wires, each formed by coating a conductor line with an insulating layer, are bound and placed on a desired application subject, is provided with: an application subject design planning step of planning a design of the application subject as a whole; a wire harness design planning step of planning a design of the wire harness so as to fit to the application subject; and a flexure life estimating step of estimating flexure life of the wire harness planned at the wire harness design planning step up to disconnection caused by extending and bending processes of the wire harness in accordance with a finite element method, and in this arrangement, the flexure life estimating step is provided with: an initial shape determining step of determining an initial shape of the wire harness; an extending and bending operation analyzing, step of: analyzing extending and bending shapes of the wire harness so as to calculate a change in curvature of the wire harness; a calculation step of an amount of change in strain for calculating an amount of change in strain of the wire harness that is a subject for estimation based upon the change in curvature obtained through the extending and bending operation; and a collation step of: making a collation on a life estimation curve that is preliminarily set based upon the amount of change in strain calculated in the calculation step of an amount of change in strain so as to predict the flexure life of the wire harness.

In accordance with the fourth or fifth aspect, in the flexure life estimation step, the individual wires are not modeled three-dimensionally as discrete structural components, but simplified them into a virtual pseudo-single wire so as to determine the entire shape; therefore, in order to calculate the initial shape and the final shape, by carrying out modeling and calculations not based upon physical properties derived from the actual construction of wire bundle, but based upon the corresponding diameter and bending elasticity of the virtual single wire, it becomes possible to greatly simplify the physical properties of wire bundle and also to calculate the resulting values. Consequently, it is possible to obtain an estimated value of flexure life that is closely approximated to the actual flexure life. Therefore, upon calculating an estimated value of flexure life through finite element method (matrix stress analyzing method) by using a computer, it becomes possible to reduce the load imposed on the computer, and also to quickly converge the estimated value.

Further, the application subject is designed and planned as a whole (application subject design planning step), and the wire harness is designed and planned so as to fit to the application subject (wire harness design planning step), and immediately after this, the flexure life estimation process is executed so as to estimate the flexure life so that in comparison with the conventional processes in which a very long time such as two or three months is required for obtaining the results of evaluation after a production of a prototype of a wire harness and flexure life evaluation tests, the present invention makes it possible to greatly reduce the period until the evaluation results have been obtained to, for example, two or three days or less than these.

Moreover, upon determining the respective initial shapes of the wire bundle, the protective tube and the external structural member, first, the initial shape of the center line of the wire bundle is used as a substitute for the initial shape of the wire bundle, and the initial shape of a virtual pipe having only a margin dimension of a margin space of the protective tube with respect to the wire bundle as an inner diameter is used as a substitute for the initial shape of the protective tube; thus, since the initial shape of the center line of the wire bundle is determined so that the center line of the wire bundle is not limited by two end portions of the virtual pipe, it is possible to direct a curvature-change reflecting the actual shape of the wire bundle and consequently to improve the estimation precision of the flexure life, in comparison with a case in which the shape of the wire bundle is limited so that the center line of the wire bundle is allowed to pass through, for example, the center point of each of the two end portions of the virtual pipe.

In accordance with the fourth or fifth aspect, in the flexure life estimation step, more specifically, the application subject design planning step and the wire harness design planning step are executed by an application subject designing station for designing and planning the application subject, and the flexure life estimating step is executed by a wire manufacturing station for manufacturing the wire harness or the application subject designing station.

In accordance with this arrangement, the flexure life estimation step can be easily executed by using a computer by the application subject designing station or the wire manufacturing station; therefore, it becomes possible to shorten the wire harness designing and developing period and also to shorten the designing and developing period of the application subject as a whole.

Preferably, in the extending and bending operation analyzing step in the flexure life estimating step, the change in curvature of the center line of the wire bundle is used as a substitute for the change in curvature of the wire bundle.

More preferably, in the flexure life estimating step, the life estimation curve represents correlation between the amount of change in strain and the number of bending processes with respect to a single wire that is obtained by actually measuring the number of bending processes up to disconnection by repeatedly bending the single wire with respect to a plurality of amounts of change in strain; and in the calculation step of an amount of change in strain in the flexure life estimating step, a virtual line member, formed by subjecting the respective bending modulus of elasticity of the conductor line and the insulating layer to weighting processes and averaging processes by using ratios of cross-sectional areas, is assumed, and on the assumption that the virtual line member serves as one of the wires, supposing that the bending radius is $R_1$ in any one of the wires in the furthest bent state at the position that is subjected to the greatest change in bending within an area in which the virtual line member is subjected to bending, that the bending radius is $R_2$ in the single wire in the furthest extended state, and that the radius of any one of wires that has the greatest difference between the value $R_1$ and the value $R_2$ is r, the amount of change in strain ($\Delta\epsilon$) is calculated by the following equation:

$$\Delta\epsilon = r \cdot (1/R_1 - 1/R_2)$$

With this arrangement, a single wire is subjected to bending processes and the correlation between the amount of change in strain and the actual measured values is preliminarily obtained, and with respect to the wire having the greatest amount of change in strain in the wire bundle serving as a subject for estimation or a virtual single wire formed by converting the wire bundle into a single wire model, the amount of change in strain is calculated by the finite element method, and the calculated amount of change in strain of the wire bundle to be estimated is collated with the above-mentioned correlation so that the flexure life of the wire bundle to be estimated is estimated; therefore, independent of product conditions of the wire bundle, it becomes possible to accurately estimate the flexure life.

More preferably, in the initial shape determining step of the flexure life estimating step, the initial shape of the wire harness is determined based upon at least the diameter of the wire harness, with the diameter of the wire harness being calculated through a predetermined arithmetic expression based upon the number and diameters of a plurality of kinds of wires constituting the wire harness.

In accordance with this arrangement, the diameter of the wire harness is calculated through a predetermined arithmetic expression based upon the number and diameters of a plurality of kinds of wires constituting the wire harness, and based upon the diameter of the wire harness, the initial shape of the wire harness is determined; therefore, the operator only needs to input the kinds and the number of wires to a computer so as to obtain the initial shape of the wire harness. Thus, the flexure life estimation step can be easily executed by using a computer by the application subject designing station or the wire manufacturing station; therefore, it becomes possible to shorten the wire harness designing and developing period and also to shorten the designing and developing period of the application subject as a whole.

More preferably, in the initial shape determining step of the flexure life estimating step, the margin dimension is found by subtracting the diameter of the wire harness from the inner diameter of the protective tube, and the diameter of the wire harness is calculated through a predetermined arithmetic expression based upon the number and diameters of a plurality of kinds of wires constituting the wire harness.

In accordance with this arrangement, the diameter of the wire harness is calculated through a predetermined arithmetic expression (claim 15) based upon the number and the diameters of a plurality of kinds of wires constituting the wire harness, and the margin dimension is found by subtracting the diameter of the above-mentioned wire harness from the inner diameter of the protective tube; therefore, the operator only needs to input the kinds and the number of wires to a computer so as to obtain the margin dimension. Thus, the flexure life estimation step can be easily executed by using a computer by the application subject designing station or the wire manufacturing station; therefore, it becomes possible to shorten the wire harness designing and developing period and also to shorten the designing and developing period of the application subject as a whole.

Preferably, supposing that the respective wires constituting the wire harness have a diameter of $d_v$, that the number of the respective wires having the diameter $d_v$ is $N_v$, and that a predetermined coefficient is $a_i$, the diameter $D_x$ of the wire harness is calculated by the following equation:

$$D_0 = \left\{ \sum_{v=1}^{m} (d_v^2 \times N_v) \right\}^{1/2} \quad \text{[Equation 3]}$$

$$Dx = \sum_{i=1}^{n} (a_i \times D_0^1)$$

More preferably, a program for allowing a computer to execute the respective steps within the flexure life estimating step in order to realize the flexure life estimating step on the computer in a wire harness designing method disclosed in any one of these claims One of the objectives of the present invention is to provide a wire harness designing method and techniques related thereto which, with respect to designing of a wire harness of cars, eliminate the necessity of carrying out the production of prototypes and the flexure evaluation tests, and consequently shorten the developing period of cars.

Moreover, another objective of the present invention is to provide a flexure life estimating method of a wire harness which, in the case of estimating the flexure life of a wire bundle within a grommet by using a finite element method, easily carries out a modeling process, and reduces the calculation processing load of a computer relating to the finite element method.

The other objective of the present invention is to provide a flexure life estimating method of a wire harness that is applied to a case in which at low temperatures, the inner conductor section has a disconnection prior to the occurrence of a crack in the insulating layer, and that can estimate the flexure life efficiently.

These and other objects, features, aspects and advantages of the present invention will become more apparent from the following detailed description of the present invention when taken in conjunction with the accompanying drawings.

DESCRIPTION OF THE PREFERRED EMBODIMENTS

{First Preferred Embodiment}

Figure 1:
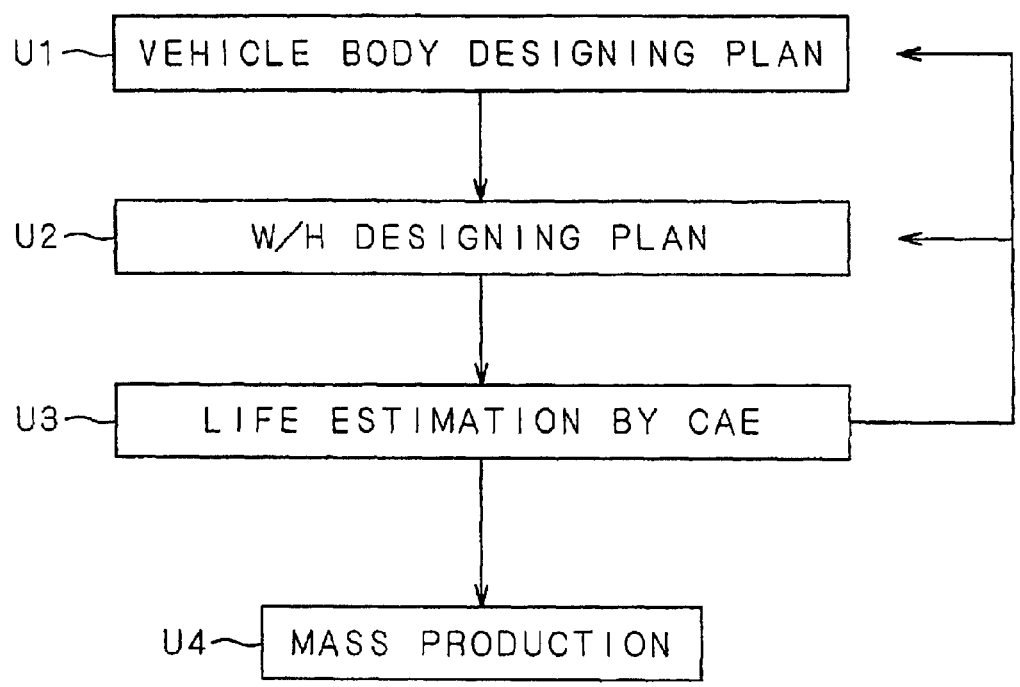
FIG. 1 is a flow chart that shows a processing sequence of a wire harness designing method in accordance with a first preferred embodiment of the present invention.

FIG. 1 shows a designing method of a wire harness (in this case, wire bundle) in accordance with one preferred embodiment of the present invention. In the initial stage of the development and designing of a wire bundle in which wire harnesses are arranged on a subject (application subject), this wire harness designing method makes it possible to quickly execute estimation of flexure life of the designed wire bundle in accordance with a sequence defined by a software program preliminarily stored in a computer. In the following description, a vehicle body is exemplified as an application subject of the wire bundle.

First, a designing plan is formed with respect to a vehicle body as a whole serving as an application subject of a wire bundle at step U1 (application subject designing and planning process).

At the next step U2, a designing plan is formed with respect to a wire bundle (wire harness: represented as "W/H" in FIG. 1) so as to make it matched to the vehicle body (application subject) (wire-harness designing and planning process).

Then, at the next step U3, based upon the design of the wire bundle planned at step U2, the life estimation of flexure of the wire-bundle is simulated by using a CAE (computer-aided engineering) method, and the results of the simulation are readily fed back to step U1 (vehicle body designing plan) and step U2 (wire bundle designing plan).

The processes of these steps U1 to U3 are repeated until the required flexure endurance of the wire bundle has been obtained, and at the time when positive examination results have been finally obtained, the corresponding mass production is started (step U4).

Figure 29:
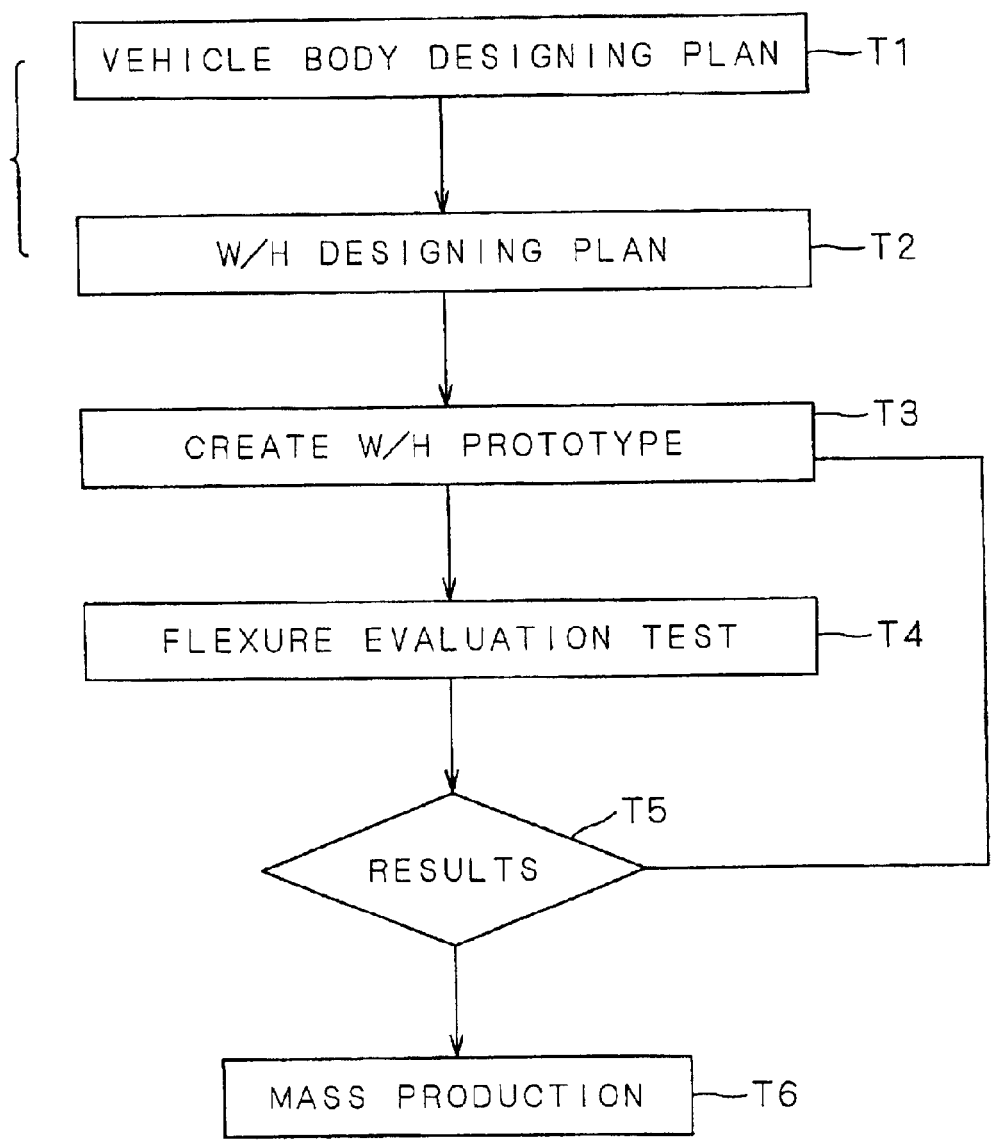
FIG. 29 is a flow chart that shows a conventional wire harness designing method.

Different from a conventional wire-harness (in this case, wire bundle) manufacturing operation in which processes such as a manufacturing process of a prototype (step T3 in FIG. 29) and a flexure estimation test (step T3 in FIG. 29) that require long time, this method makes it possible to omit these processes. Moreover, conventionally, only the manufacturing maker (wire manufacturing station) of wire bundles can carry out the life estimation of flexure that is step U3 of the corresponding wire bundle; however, in the present preferred embodiment, since the life estimation of flexure is easily carried out by using a computer, even a designing and manufacturing maker (application subject designing station) of the application subject in which the wire bundle is applied and used, it is possible to carry out the life estimation of flexure easily by using a computer with respect to step U3. Therefore, it becomes possible to shorten the developing period while ensuring sufficient reliability in the initial designing stage.

Here, a detailed explanation will be given of a method of the life estimation of flexure of a wire harness in the CAE process at step U3.

Figure 2:
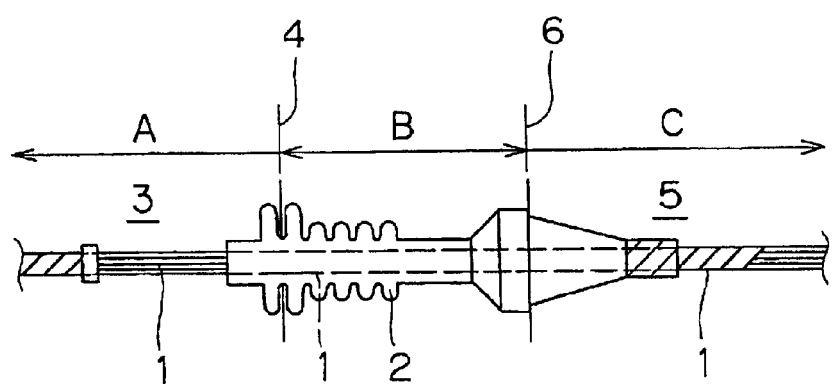
FIG. 2 is a drawing that shows a wire harness used in a door portion of a car.

For example, FIG. 2 is a side view that shows a wire bundle 1 and a grommet (protective tube) 2 that form designing subjects. Here, for example, in the above-mentioned step U3, in the case when a wire bundle passes through the inside of a grommet 2 that is placed at B in the vicinity of a hinge portion between a predetermined position (door panel) 4 of a door 3 (an area indicated by symbol A in FIG. 2) and a predetermined position (body panel) 6 of a body 5 (an area indicated by symbol C in FIG. 2), an explanation will be given of a case in which the life estimation of flexure of wire bundle 1 is carried out when wire bundle 1 is subjected to extending and bending changes in accordance with the opening and closing operations of door 3. Here, in this specification, door 3, door panel 4, body 5 and body panel 6 are generally referred to as an external structural component.

The inventors, etc. of the present invention have made extensive research effects with respect to factors that control the flexure life of wire bundle 1. Consequently, in particular, at low temperatures, when a fatigue crack is generated in an insulating layer of each wire, the conductor section at the portion having the crack is more susceptible to a local stress; therefore, it has been found that disconnection in each wire of wire bundle 1 is mainly controlled by the fatigue fracture in the insulating layer coating the conductor section, and that the fatigue fracture of the insulating layer has a strong correlation with the amount of change in the surface strain. In other words, it has been found that there is a strong correlation between the flexure life of wire bundle 1 and the amount of change in strain of the surface of an insulating layer at the time of being bent. Here, when wire bundle 1 is actually attached to the car door 3, etc., it is attached thereto in various shapes such as an S-letter shape and a U-letter shape. Depending on the shapes, the way how a stress is exerted on wire bundle 1 is also changed. However, it has been found that, in spite of the various shapes in which the wire bundle 1 is placed, the correlation between the flexure life of wire bundle 1 and the amount of change in strain is not dependent on the shape of wire bundle 1, and it is maintained constant in a wide range of the flexure shape.

Therefore, by preliminarily finding the correlation between the flexure life and the amount of change in strain of wire bundle 1 through experiments, it becomes possible to estimate the flexure life of the wire bundle, etc. by analyzing only the amount of change in strain of wire bundle 1 under various product conditions.

In the case when the amount of change in strain is analyzed on wire bundle 1, it is effective to use a computer based upon finite element method; however, since the wire bundle 1 includes a plurality of wires, and since the shape of grommet 2 is complicated, when the analysis is carried out based upon finite element method while strictly modeling these shape and physical properties (bending rigidity), the calculation processing load on the computer becomes greater. Therefore, the objective of present invention is to provide a method of estimation of flexure life which can maintain high estimation precision of flexure life while simplifying the finite element model of each structural component and reducing the calculation processing load of the computer.

More specifically, the method of estimation of flexure life is provided with a curvature value calculation process (FIG. 3) for finding a curvature value of a wire bundle 1 by using the finite element method and an estimated life outputting process for obtaining the estimated life of wire bundle 1 based upon the resulting curvature value of wire bundle 1. The following description will, discuss respective processes in detail.

<1. Curvature Value Calculation Process>

Figure 3:
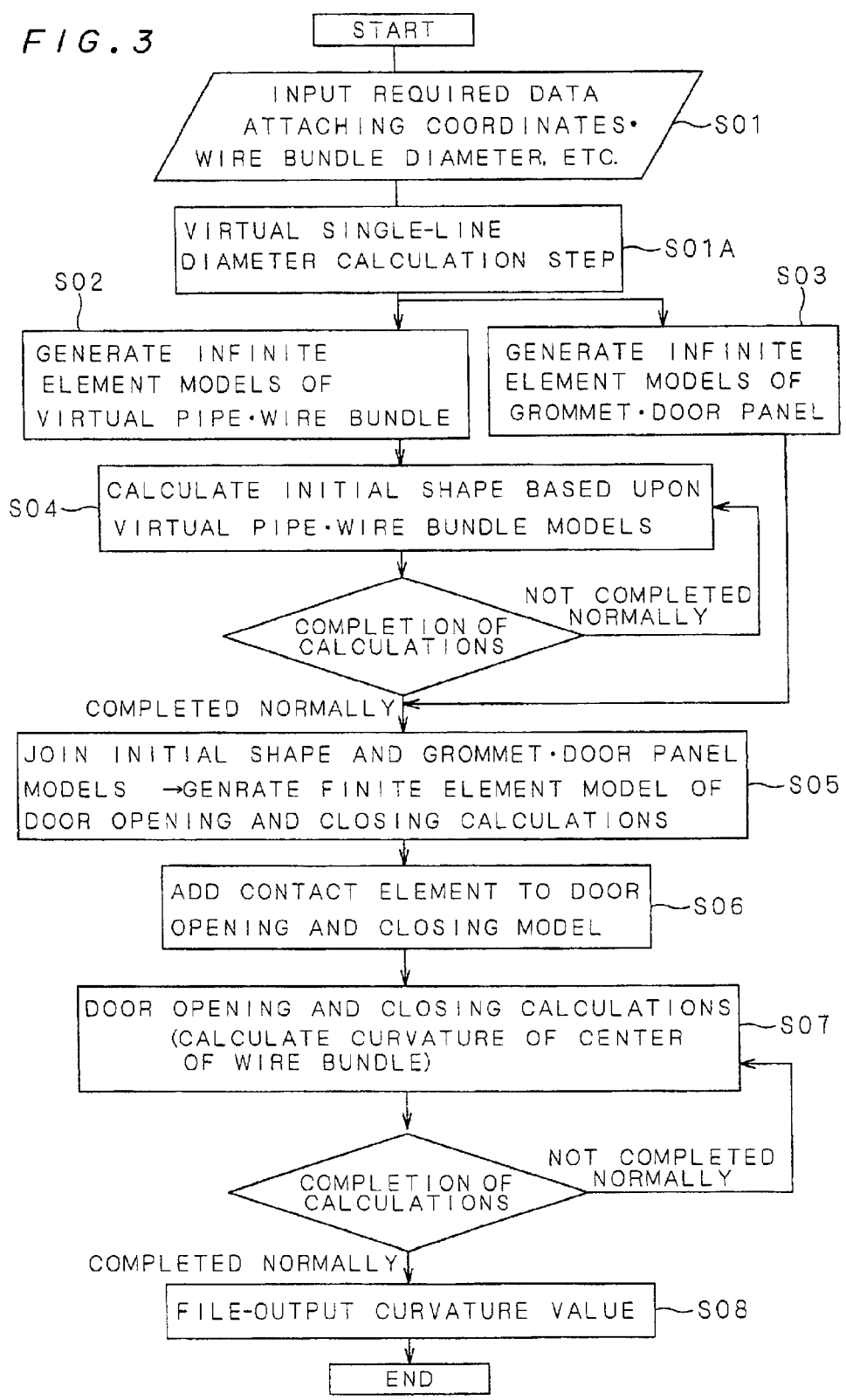
FIG. 3 is a flow chart that shows a curvature value calculation process in a flexure life estimating process in accordance with the first preferred embodiment of the present invention.

A curvature value calculation process is a process which finds the curvature radius R of each of the door opened state and door closed state of a virtual single wire 11 (see FIG. 16) that simulates a wire bundle 1 through a computer calculation process using finite element method, and is provided with a parameter input step (step S01) for inputting parameters in a computer as shown in FIG. 3, an initial state determining process (step S02, S04) for determining the initial shape of each structural component required for calculations in the finite element method, an extending and bending operation analyzing process (step S03, S05 to S08) that carries out an operation analysis at the time when a wire bundle 1 inside grommet 2 is extended and bent in response to opening and closing operations of door 3.

1-1 Parameter Input Process

In the parameter input process, first, at step S01, parameters required for the analyzing process in the succeeding steps are inputted.

Specific items of the parameters include attaching coordinates of a securing point to which wire bundle 1 is secured, attribute information of wire bundle 1, attribute information of grommet 2, the opening and closing angles of door 3, and temperature conditions.

Figure 4:
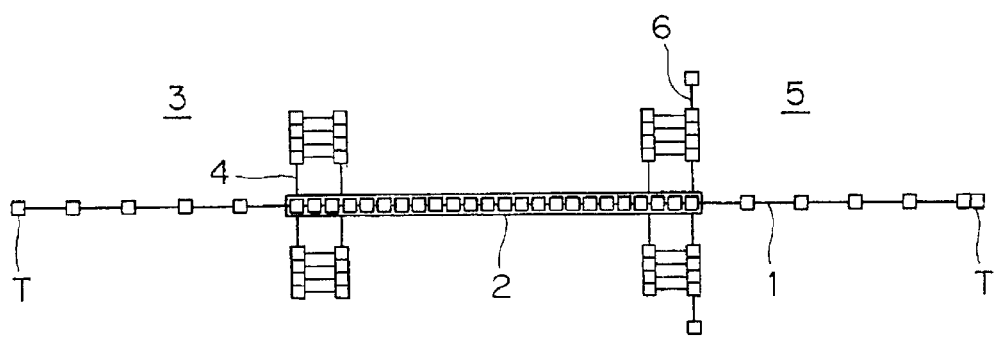
FIG. 4 is a drawing that shows a state in which respective coordinate positions of a center line of a door panel and a body panel of a car in the closed state and a wire bundle are specified.
Figure 5:
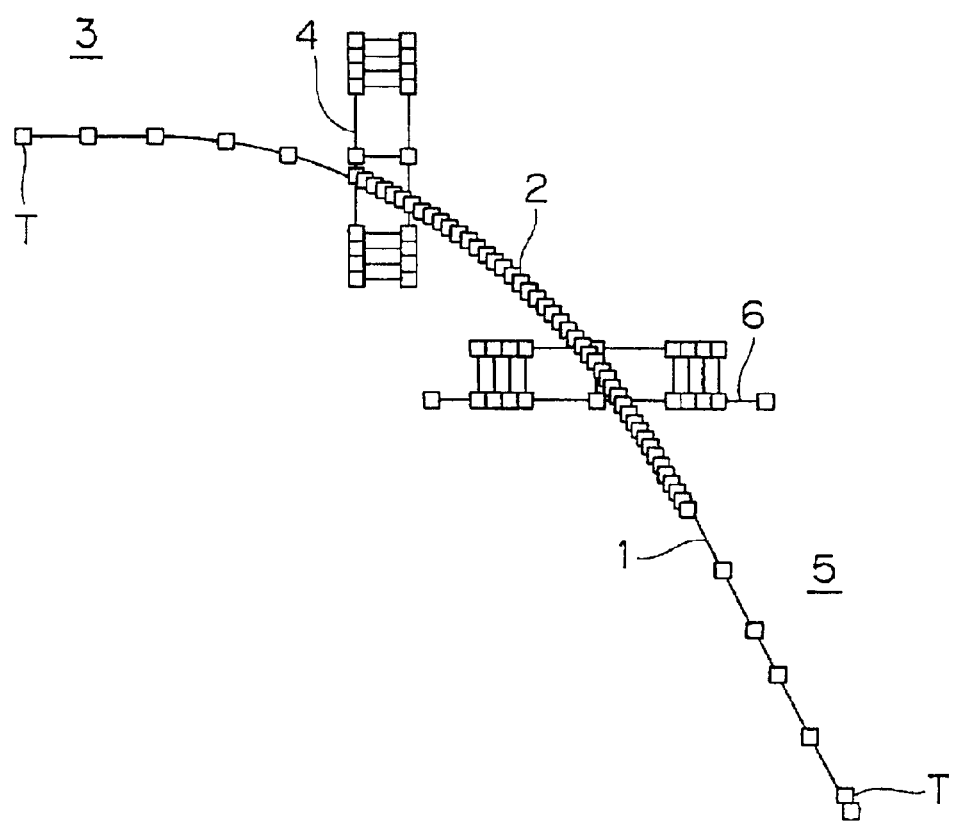
FIG. 5 is a drawing that shows a state in which respective coordinate positions of the center line of the door panel and the body panel of a car in the opened state and the wire bundle are specified.

With respect to the attaching coordinates of the securing point of wire bundle 1 to be inputted to as input parameters, for example, as shown in FIG. 4 or FIG. 5, respective coordinate positions of door panel 4 of car door 3 and body panel 6 of body 5 are specified, and with respect to these door 3 and body 5, coordinate positions to which wire bundle 1 is secured are specified by clamp T, etc., so that respective inputting operations are carried out. With respect to the input values in this case, for example, as shown in FIG. 4, by preliminarily inputting the attaching coordinates at the time of the closed state of door 3, the shape of wire bundle 1 at the time of the opened state of the door shown in FIG. 5 is found through calculations that are given following the changes of door 3 to the opened state; thus, it is not necessary to carry out the inputting operations at step S01.

With respect to the attribute information of the wire bundle 1 to be inputted as input parameters, the kinds (product numbers) of wires constituting wire bundle 1, the diameters of conductor lines within the wires, the number of the conductor lines and respective values, etc. of the bending rigidity of the respective conductor lines and the respective insulating layers are specified and inputted.

With respect to the attribute information of grommet 2, the inner diameter of the through-hole of tube-shaped grommet 2 and the length of grommet 2, etc. are specified, and inputted. Here, with respect to the rigidity of grommet 2, it is not necessary to input these. The reason for this will be explained in the following description.

In this example, the method of estimation of flexure life of the wire bundle 1 in the CAE process, literally, it is only necessary to estimate the flexure life of the corresponding wire bundle 1, and it is not necessary to estimate the flexure life of grommet 2. Moreover, in the first preferred embodiment, the objective is to find estimated values suitable for the application in a car at low temperatures, and it has been confirmed through experiments that changes in the bending rigidity of grommet 2 due to temperature changes such as normal temperature and low temperatures can be ignored in comparison with changes in the bending rigidity of the wire bundle 1, depending on the material to be used. Therefore, when the wire bundle 1 is hardened under a low temperature, the shape of wire bundle 1 is hardly regulated by the shape of grommet 2, and in contrast, the shape of grommet 2 is regulated by the shape of wire bundle 1. Consequently, it is only necessary to confirm the shape of grommet 2, and it is not necessary to provide parameters in the bending rigidity in relation to temperature changes of grommet 2; therefore, since it is possible to sufficiently estimate the flexure life of wire bundle 1 with the rigidity of grommet 2 being ignored, there is no degradation in the precision of the estimated value of flexure life of wire bundle 1 even when the physical parameters such as bending rigidity of grommet 2 are omitted from this step S01.

With respect to the opening and closing angles of door 3, the relative angle of door 3 with respect to body 5 in the closed state of door 3 and the relative angle of door 3 with respect to the body 5 in the opened state of door 3 are specified, and inputted.

Moreover, with respect to the wire bundle 1, since the value of the bending rigidity changes in response to a change in the temperature such as normal temperature and a low temperature (including temperatures corresponding to cold temperatures in winter), the temperature parameters thereof are also inputted.

Here, the respective inputted parameters are stored in a predetermined storing device, such as a hard disk drive, as data files referred to as procedure files.

The succeeding processes after the above-mentioned parameter inputting processes are executed by the CPU that is operated in a sequence specified by software programs that have been preliminarily stored in a hard disk of the computer.

1-2 Virtual Single Wire Diameter Calculation Process

As will be described later, in this preferred embodiment, a wire bundle constituted by a plurality of wires is modeled into a virtual single wire (see FIG. 16), and this is used for estimating the flexure life. Therefore, at step S01A, the diameter of virtual single wire 11 used for modeling is determined based upon the types (product numbers) of wires inputted in the parameter input process (step S01), the diameter of the conductor lines within the wires and the number of the corresponding wires.

More specifically, a list of outer diameters (finished outer diameters) including coating portions of the respective wires has been preliminarily stored in a hard disk of a computer, and in accordance of the types (product numbers) of the wires inputted in the parameter input process (step S01), the respective finished outer diameters are read out. Here, it is supposed that the kind of each of the wires is represented by a variable V (=1 to m) and the finished outer diameter of each of the wires of the kind v is represented by dv. Moreover, it is supposed that the number of the used wires v, inputted in the parameter input process (step S01), is represented by Nv. At this time, the diameter Dx of the virtual single wire used for simple-modeling the wire bundle is found from the following multi-dimensional approximation equation (1).

[Equation 4] (1)

$$D_0 = \left\{ \sum_{v=1}^{m} (d_v^2 \times N_v) \right\}^{1/2}$$

$$Dx = \sum_{i=1}^{n} (a_i \times D_0^i)$$

Here, ai (i=0, 1, 2, ..., n) in equation (1) is an inherent coefficient derived from rule of thumb, and such an equation (1) is defined by a software program preliminarily stored in a hard disk in a computer.

In this manner, upon modeling the wire bundle, at the parameter input process (step S01), the operator only needs to input the kinds and the number of wires so as to allow the computer to automatically calculate the diameter of a virtual single wire; therefore, with respect to step U3, even only within a designing and manufacturing maker (application subject designing station) of an application subject in which the wire bundle is applied and used, it is possible to easily carry out the life estimation of flexure of the wire bundle by using a computer.

Moreover, together with the virtual single wire diameter calculation process, parameters of bending rigidity of the individual wires v (conductor lines and insulating layers) serving as each structural component within wire bundle 1 preliminarily stored in a hard disk are read out beforehand. These parameters in bending rigidity are used for correctly modeling the shape of wire bundle 1 in the respective initial shape, opened state and closed state of door 3. Here, in this preferred embodiment, as will be described later, on the assumption that a simple one virtual single wire 11 (see FIG. 16) is used as wire bundle 1, the flexure life of the surface of each wire (including the insulating layer forming the coating portion) is estimated; and, for example, in the case when, for example, upon carrying out repeated life estimations of flexure, the diameter and bending rigidity (bending elasticity) of virtual single wire 11 have been preliminarily found through the previous life estimation of flexure, parameters such as the diameter and bending rigidity of virtual single wire 11 may be directly inputted.

1-3 Initial Shape Determining Step

In the initial shape determining step at the next stage, the initial shapes of a virtual pipe 9 and virtual single wire 11 (see FIG. 16) formed by simple-modeling wire bundle 1 are determined to form a finite element model.

First, at step S02, virtual pipe 9 and virtual single wire 11 are aligned in a linear state to form finite element models.

Figure 6:
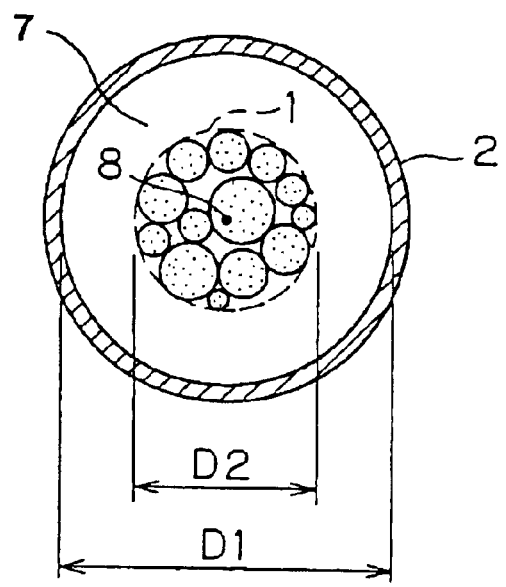
FIG. 6 is a cross-sectional view that shows the wire bundle and a grommet.

In this case, first as shown in FIG. 6, a realistic model (hereinafter, referred to as "real model") in which a wire bundle 1 having a thickness of an outer diameter D2 passes through a through hole 7 of a grommet 2 having an inner dimension of D1 is formed. In this case, the margin dimension of a margin space of grommet 2 with respect to the wire bundle 1 is a value (D1−D2) obtained by subtracting outer diameter D2 of wire bundle 1 from dimension D1 of the inner diameter of grommet 2.

Figure 7:
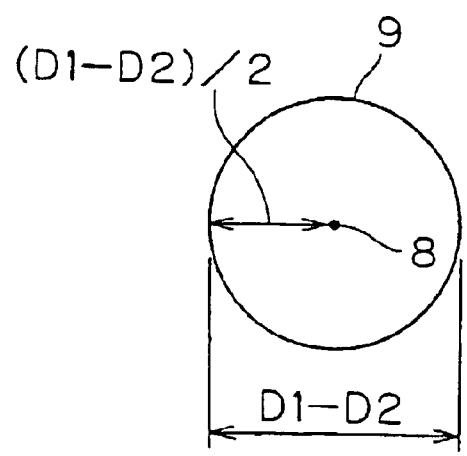
FIG. 7 is a cross-sectional view that shows the center line and a virtual pipe of the wire bundle.

Here, in the stage for determining the initial shape of the wire bundle 1, since the procedure for determining the shape becomes complex when its thickness (outer diameter D2) is taken into consideration, a virtual model in which only the center line 8 having no thickness is taken into consideration as the center axis of the wire bundle 1 as shown in FIG. 7 is determined, in addition to the above-mentioned real model.

Figure 8:
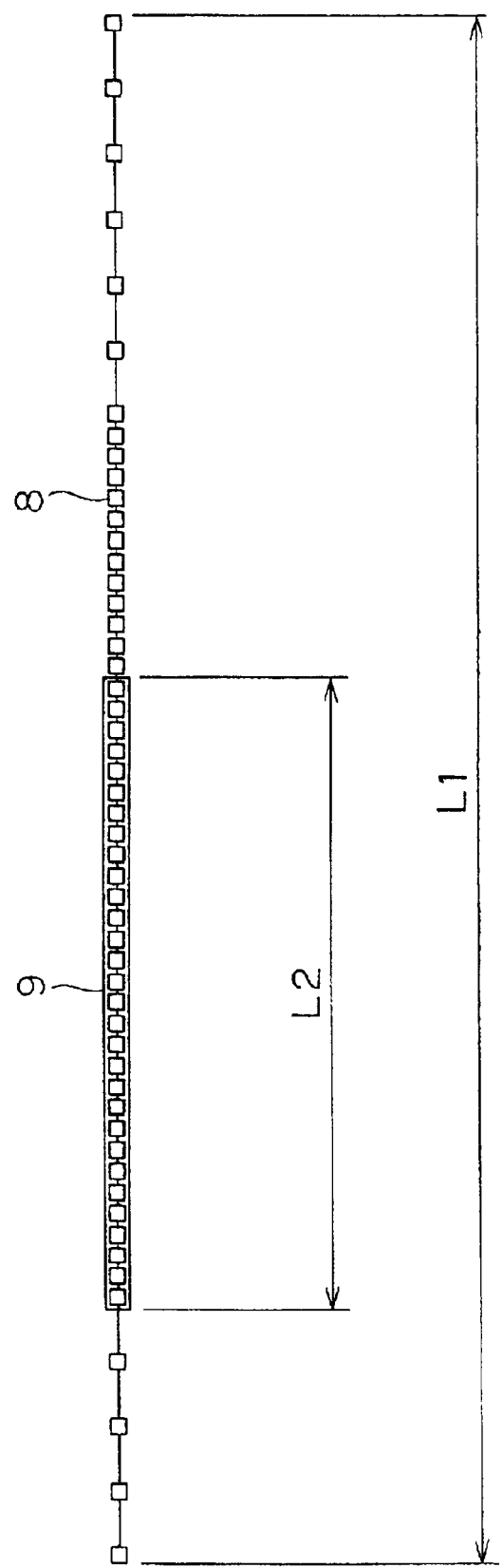
FIG. 8 is a drawing that shows a state in which the center line and the virtual pipe are displayed on a virtual space.

In the case of this virtual model, with respect to the distance of the gap between the outer surface of wire bundle 1 and the inner circumferential face of grommet 2, it is of course desirable to apply a dimension close to the actual dimension thereof. Therefore, the value Dx (see equation (1)) found at step S01A is adopted as an approximate diameter D2 of the wire bundle, and as shown in FIG. 7, a virtual pipe 9, which is apart from center line 8 having no thickness by the same distance as the distance of the actual gap {(D1−D2)/2} is assumed. The inner diameter of virtual pipe 9 is (D1−D2). This value is coincident with the above-mentioned margin dimension of the margin space. Here, the actual model and the virtual model in this step S02 are aligned so as to make center line 8 of wire bundle 1 coincident with the center line of virtual pipe 9. In this case, the shape of the linear virtual pipe 9, determined here, is shown in FIG. 8. Reference number L1 in FIG. 8 represents the length dimension of wire bundle 1 (and center line 8 thereof) to be used in the analysis calculating process in the method of estimation of flexure life, and a desired value, which is set, at least, longer than the length of a portion that might be deformed by the door opening and closing operations, is applied. Moreover, reference number L2 is a length dimension of the actual grommet 2, which is represented in the Figure as the length dimension of a virtual pipe 9.

Here, with respect to the actual model and the virtual model, element divisions are preliminarily carried out by setting an infinite element mesh with predetermined fine gaps. Here, the shape of center line 8 of wire bundle 1 inside virtual pipe 9 is very important in carrying out the life estimation of flexure of center line 8 of wire bundle 1. For this reason, at the time of carrying out the element divisions, the finite element mesh of center line 8 of wire bundle 1 inside virtual pipe 9 is set finer than the finite element mesh of center line 8 of wire bundle 1 that is set outside the virtual pipe 9.

Here, the operation of this step S02 is automatically calculation-processed by CPU of the computer based upon the parameters inputted at step S01.

Figure 9:
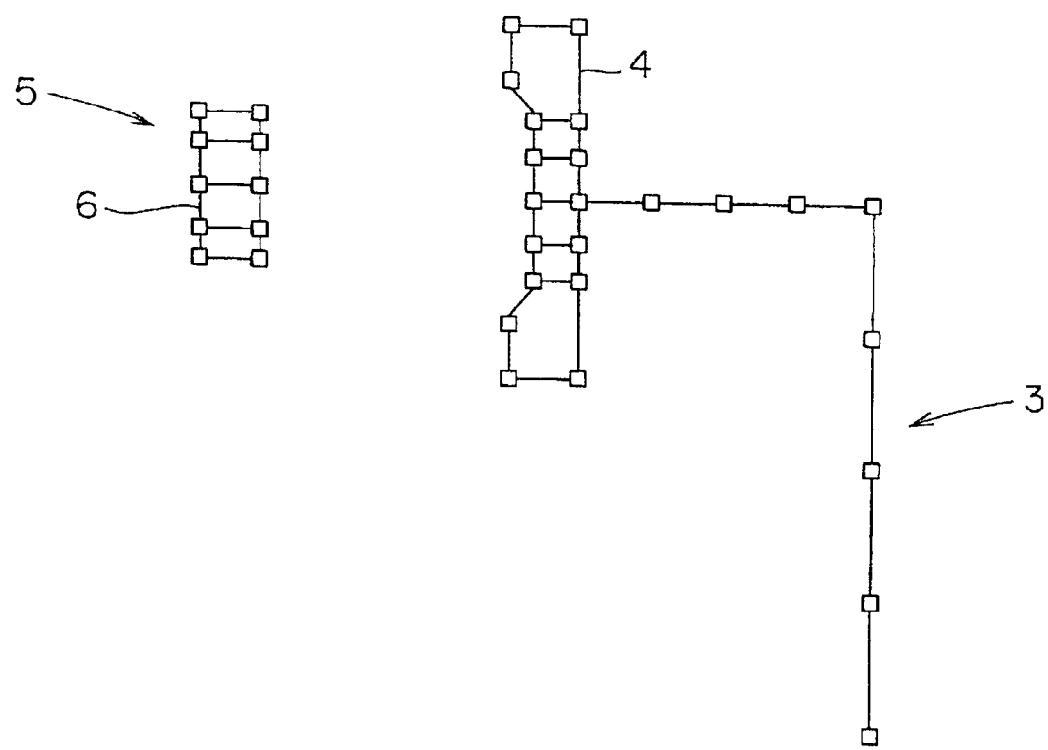
FIG. 9 is a drawing that shows a state in which the door and the body are displayed on a virtual space.

Next, at step S03, as shown in FIG. 9, based upon coordinate positions corresponding to the actual states of door panel 4 of door 3 and body panel 6 of body 5, these finite element models are formed. In this case, with respect to the initial shapes of door panel 4 and body panel 6, for example, the shapes at the time of the door closed state are applied. Moreover, with respect to door 3 and body 5, the positions of clamp T of wire bundle 1 are respectively specified. The coordinate positions of door panel 4 and body panel 6, determined here, are used for determining the attaching positions (grommet position) of grommet 2 and virtual pipe 9. The operation at this step S03 is automatically calculation-processed in CPU of the computer based upon the parameters inputted at step S01.

Figure 10:
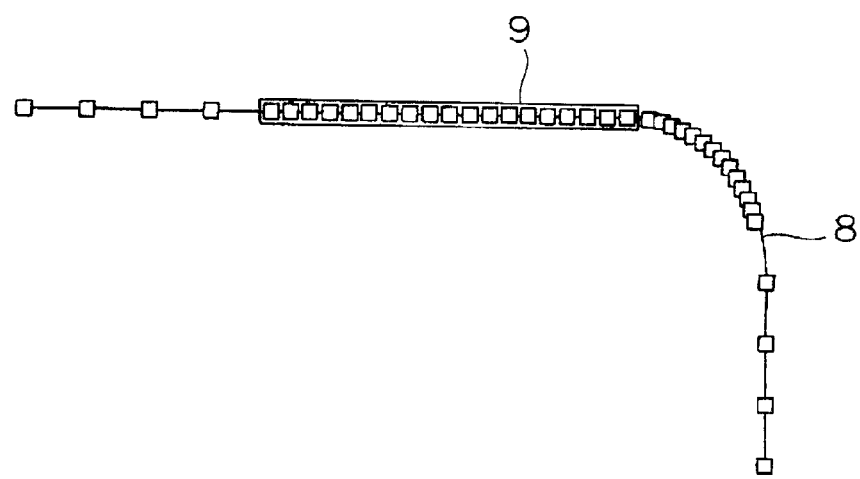
FIG. 10 is a drawing that shows a state in which the shapes of the center line of the wire bundle and the virtual pipe are made to fit to the door and the body.

At the next step S04, the initial shapes of virtual pipe 9 and wire bundle 1 related to models of center line 8 are calculated. More specifically, virtual pipe 9 and wire bundle 1 formed at the above-mentioned step S02 are transformed so as to fit to the coordinate positions of door panel 4 and body panel 6 formed at step S03 so as to determine the initial shape of center line 8 of virtual pipe 9 and wire bundle 1 as shown in FIG. 10.

Next, a detailed explanation will be given of a determining method of the initial shape of center line 8 of wire bundle 1.

Figure 11:
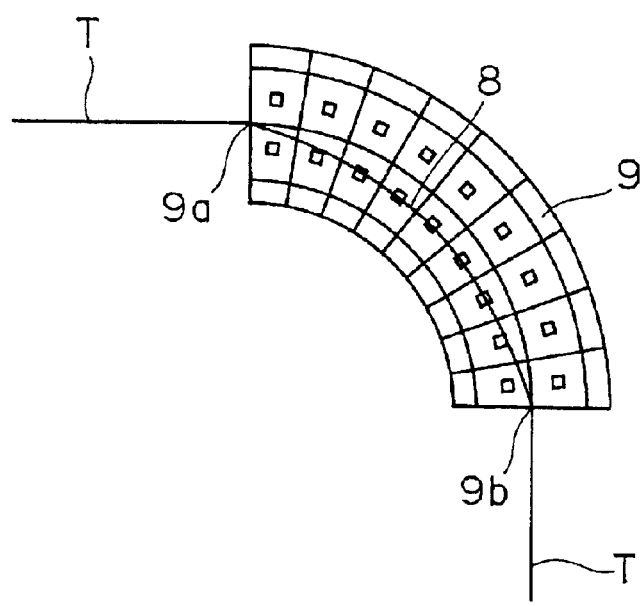
FIG. 11 is a drawing that shows a positional relationship between the center line of the virtual pipe and the wire bundle in a proposed example.
Figure 12:
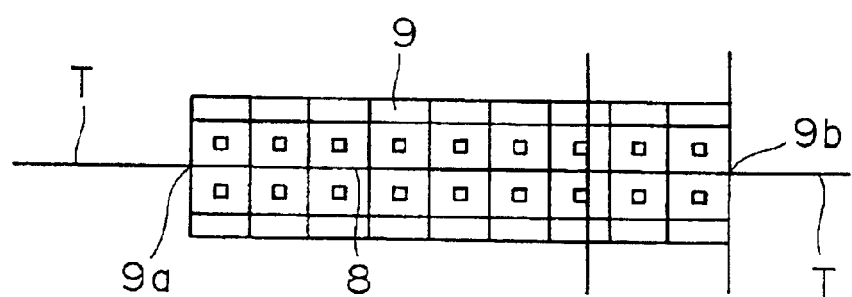
FIG. 12 is a drawing that shows a positional relationship between the center line of the virtual pipe and the wire bundle in the proposed example.

For example, as shown in FIGS. 11 and 12, in the case when center line 8 corresponding to the shape of wire bundle 1 penetrates the inside of virtual pipe 9 corresponding to the inner circumferential shape of grommet 2, a method may be proposed in which the shape of center line 8 is determined so as to allow center line 8 of wire bundle 1 to pass through central points 9a, 9b on the two end portions of virtual pipe 9. However, since center line 8 of wire bundle 1 is placed in the inner space of virtual pipe 9 with a dimensional margin (which corresponds to the fact that wire bundle 1 is placed in the inner space of grommet 2 with a margin), center line 8 of wire bundle 1 is not necessarily allowed to pass through central points 9a, 9b on the two end portions of virtual pipe 9. In contrast, in most cases, when virtual pipe 9 and central line 8 of wire bundle 1 are curved as shown in FIG. 11 in the opened state of door, center line 8 of wire bundle 1 is regulated by the position of clamp T, with the result that it has an offset from center points 9a, 9b on two end portions of virtual pipe 9. In this manner, if center line 8 of wire bundle 1 is modeled into a shape different from the actual shape, and if this is used for estimating the flexure life, the resulting estimated value becomes greatly different from the actual flexure life of wire bundle 1.

Figure 13:
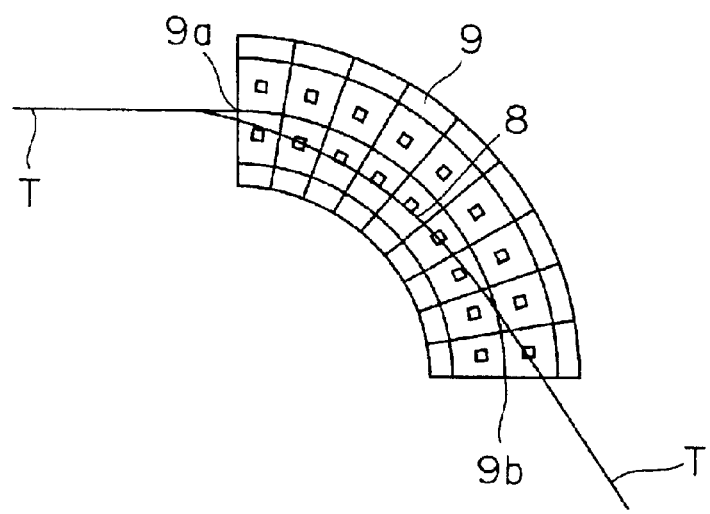
FIG. 13 is a drawing that shows a positional relationship between the virtual pipe and the center line of the wire bundle in accordance with the first preferred embodiment of the present invention.
Figure 14:
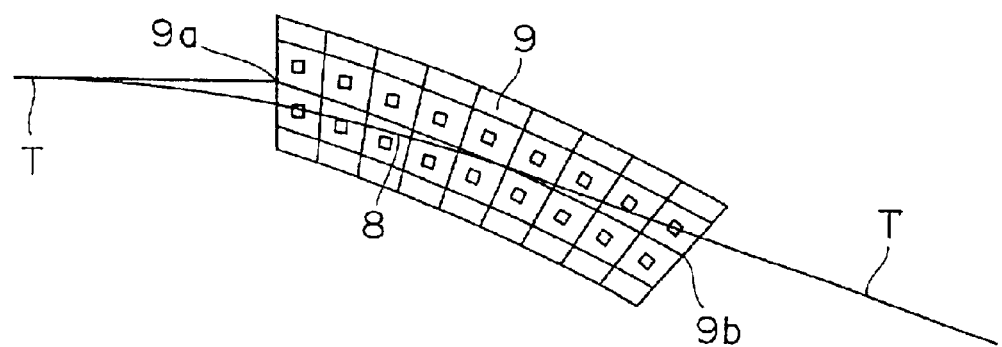
FIG. 14 is a drawing that shows a positional relationship between the virtual pipe and the center line of the wire bundle in accordance with the first preferred embodiment of the present invention.

For this reason, in this preferred embodiment, center line 8 of wire bundle 1 is modeled with the existence of virtual pipe 9 being virtually ignored (hereinafter, referred to as "completely free model"). In other words, in the case when center line 8 of wire bundle 1 (corresponding to the shape of wire bundle 1) and virtual pipe 9 (shape of grommet 2) are aligned in a linear state, as illustrated in FIG. 12, an arrangement is made so that center line 8 of wire bundle 1 is allowed to pass through center points 9a, 9b of the two end portions of virtual pipe 9; however, in the case when virtual pipe 9 is curved, as illustrated in FIGS. 13 and 14, a shape is determined so that, independent of the coordinate positions of center points 9a, 9b of the two end portions of virtual pipe 9, center line 8 of wire bundle 1 is only regulated by the positions of clamp T of door 3 and body 5 that secure wire bundle 1.

However, in the case when, as described earlier, virtual pipe 9 is curved due to the opened state of door 3, it is supposed that the surface of wire bundle 1 comes into contact with the intermediate position on the inner circumferential portion of the corresponding actual grommet 2, and only in this case, the shape of wire bundle 1 is limited by the shape of grommet 2. By taking this fact into consideration, in the present preferred embodiment, the actual model is used at step S06, which will be described later, and with respect to virtual single wire 11 (see FIG. 16) and grommet 2, the shapes are limited by taking into consideration the door opening and closing operations. However, such corrections are not executed at this step S04, but executed on step S06 which will be described later.

In this manner, in the case when center line 8 of wire bundle 1 is allowed to penetrate the inside of virtual pipe 9, calculations are executed based upon finite element method by using the completely free model with the existence of virtual pipe 9 being ignored (that is, a model in which the shape of center line 8 of wire bundle 1 is not subjected to influences from virtual pipe 9); therefore, when a wire harness is applied as center line 8 of wire bundle 1, it is possible to properly approximate the calculated value (estimated value) of flexure life to the value of actual flexure life, in comparison with conventional calculations carried out on the assumption that it is secured on the center of each of the terminals of virtual pipe 9.

Moreover, since it is possible to omit computer analyzing processes of virtual pipe 9 that are carried out based upon finite element method, it becomes possible to greatly reduce the load of calculation process in the computer. Moreover, since it becomes possible to eliminate the process for dividing virtual pipe 9 by using finite element meshes, the work load can be reduced greatly.

1-4 Extending and Bending Operation Analyzing Step

Figure 15:
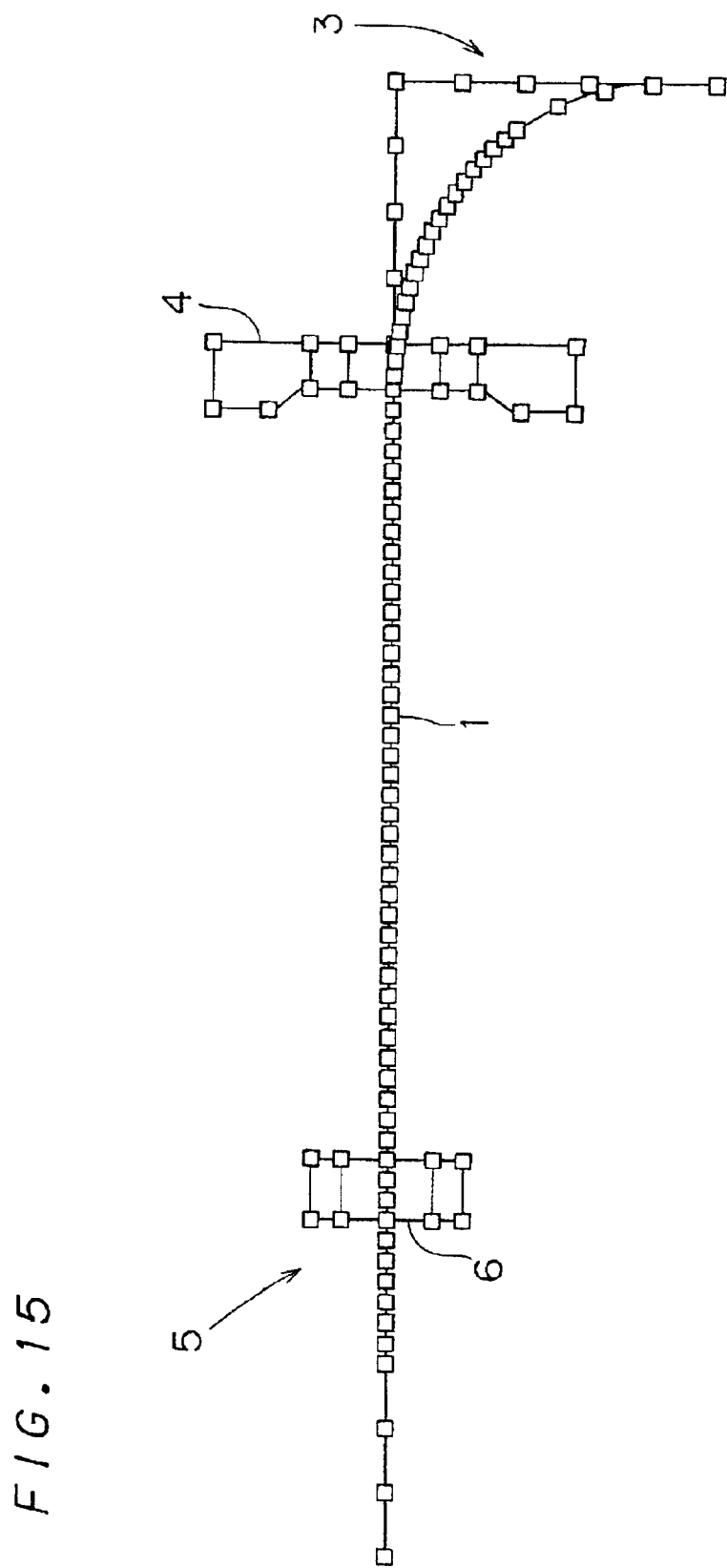
FIG. 15 is a drawing that shows a state in which the center line of the wire bundle and the virtual pipe are joined to the door and the body.

At step S05, models of the initial shapes of door panel 4 and body panel 6 formed at the above-mentioned step S03 and a model of the initial shape of center line 8 of virtual pipe 9 and wire bundle 1 formed at the above-mentioned step S04 are combined with each other as shown in FIG. 15 so as to form a finite element model used for door opening and closing calculations. More specifically, attaching coordinates of securing points inputted at step S01 are plotted on door panel 4 and body panel 6 formed at step S03, and the model of center line 8 of wire bundle 1 formed at step S04 are overlapped on the attaching coordinates of these securing points.

Next, at step S06, a contact element is added to the door opening and closing model. In this case, a real model is used. However, if all the wires in wire bundle 1 are respectively formed into structural components, the analyzing calculations in the following step become complex so that a virtual single wire (virtual line member) 11, shown in FIG. 16, that is assumed based upon general physical properties of wire bundle 1 is adopted. In this virtual single wire 11, the bending modulus of elasticity of the metal materials in the conductor portions in a plurality of wires in wire bundle 1 and the bending modulus of elasticity of the insulating materials of the coating layer are subjected to weighting processes, and averaged based upon the ratio of cross-sectional areas, and assuming that a virtual material in which the metal material of the conductor portion and the insulating material of the coating layer are averaged is prepared, a virtual single wire 11 made of this virtual material is prepared. Then, based upon the fact that this virtual single wire 11 comes into contact, with being regulated by grommet 2, the contact element is defined while taking into consideration the diameter Dx (see step S01A) of virtual single wire 11 within the grommet 2 as well as taking its space occupying rate into consideration, and the shape of virtual single wire 11 is corrected. Here, with respect to a specific defining method of the contact element, since it is the same as the defining method of a contact element in a general finite element model; the description thereof is omitted for convenience of explanation.

Next, at step S07, based upon the opening and closing angles of door 3 inputted at step S01, the curvature radius R of center line 8 of wire bundle 1 is calculated with respect to each of the opening state and the closing state of door 3 based upon center line 8 of wire bundle 1 in the virtual model.

Then, at step S08, based upon curvatures calculated at step S07, the amount of change in curvature between the furthest extended state and in the furthest bent state in the length direction of center line 8 of wire bundle 1 is calculated. The results of calculation of this amount of change in curvature are stored in a predetermined storing device such as a hard disk drive, etc., as data in a data file referred to as a curvature value file.

<2. Estimated Life Outputting Process>

Figure 17:
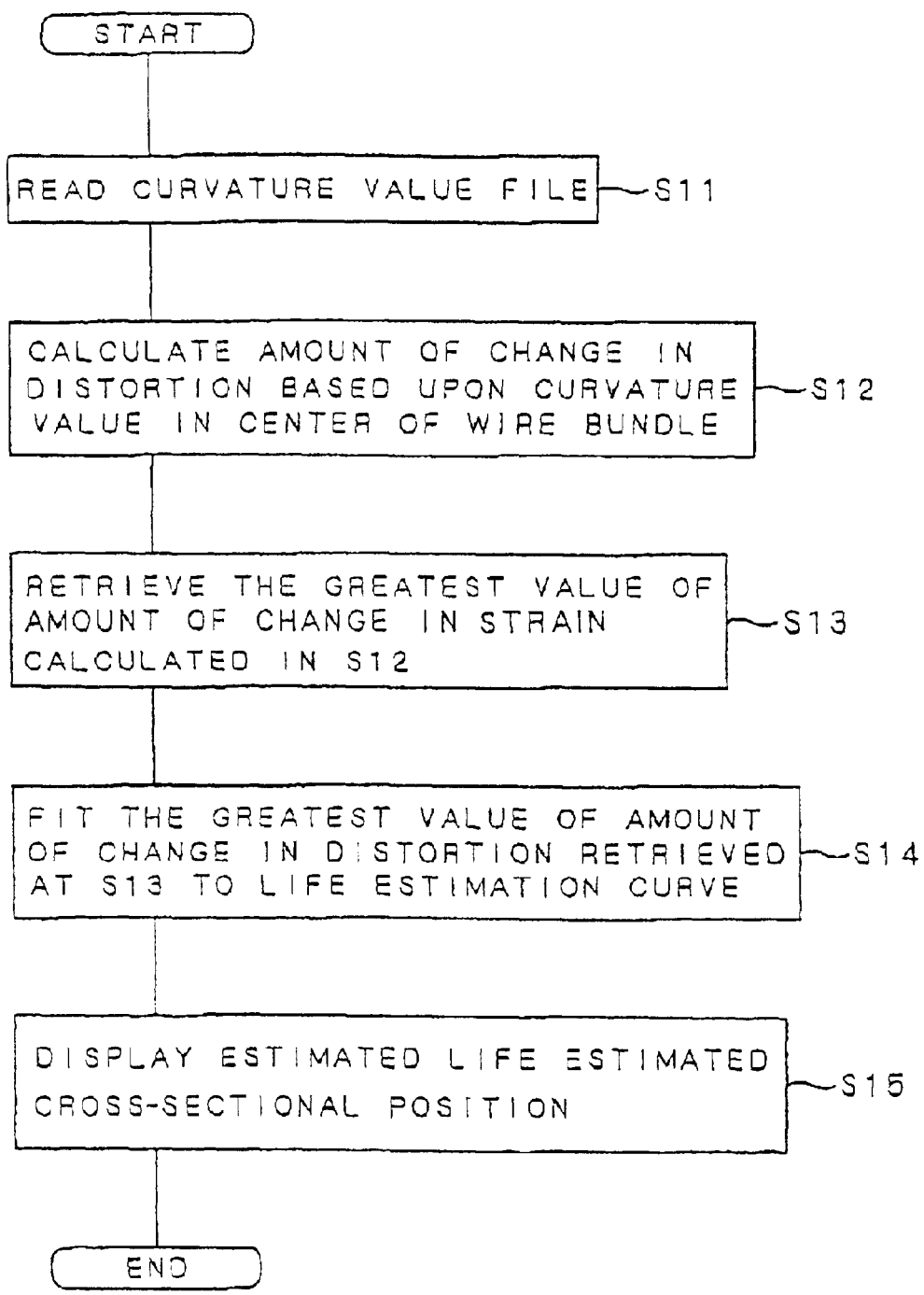
FIG. 17 is a flow chart that shows an estimated life outputting step in a wire harness flexure life estimating method in accordance with the first preferred embodiment of the present invention.

FIG. 17 is a flow chart that shows a processing sequence of the estimated life outputting process. Here, with respect to a pre-stage before the processing sequence shown in FIG. 17, it is necessary to preliminarily obtain a master curve (life estimating curve) that indicates a correlation between the flexure life of wire bundle 1 and the amount of change in strain.

2-1 Master Curve (Life Estimation Curve) Obtaining Process (Pre-stage)

Figure 18:
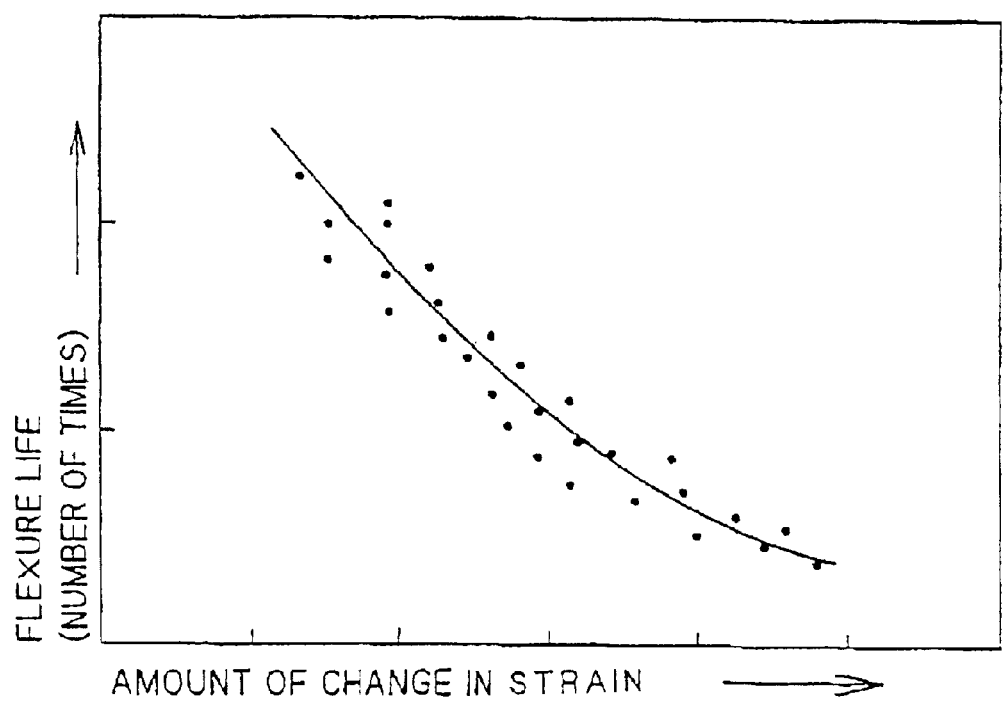
FIG. 18 is a drawing that shows a master curve.

In the obtaining process of the master curve (life estimation curve), with respect to a single wire, based upon the value of the curvature radius in the curvature value calculation process obtained through the above-mentioned finite element method, the amount of change in strain of the single wire is found, and the value of this amount of change in strain and the flexure life of the corresponding single wire obtained as a result of the experiment are plotted on predetermined graph coordinates; thus, an approximate correlation curve as shown in FIG. 18 is found to form the master curve (life estimation curve). The axis of abscissas in this Figure represents the amount of change in strain of the surface of the insulating layer, and the axis of ordinate represents the flexure life.

Here, the following description will discuss the amount of change in strain in a single wire. It is supposed that a single wire, formed by a conductor line coated with an insulating layer, has a radius of r. This single wire is subjected to a bending strain, and supposing that its bending radius is R, the curvature K is represented by K=1/R. In this case, strain ε appearing on the surface of the insulating layer of the single wire is represented by the following equation:

$$\varepsilon = 2\pi(R+r)/2\pi R - 1 \quad (2)$$
$$= (R+r)/R - 1$$

With respect to a single wire that is placed at a position that is subjected to bending of door 3, etc., supposing that the bending radius is $R_1$ in the single wire in the furthest bent state at the position that is subjected to the bending, that the bending radius is $R_2$ in the single wire in the furthest extended state, and that the amount of change in strain on the surface of the insulating layer is Δε, when the single wire is repeatedly extended and bent between the furthest extended state and the furthest bent state, Δε is represented by the following equation (3):

$$\Delta\varepsilon = (R_1 + r)/R_1 - (R_2 + r)/R_2 \quad (3)$$
$$= r \cdot (1/R_1 - 1/R_2)$$
$$= r \cdot \Delta K$$

Here, in equation (3), ΔK represents the amount of change in curvature when the single wire is subjected to repeated bending, and this value is calculated through a curvature value calculation step based upon finite element method. The calculated value ΔK is listed with respect to each portion of the single wire, and ΔK having the greatest value is adopted so that the amount of change in strain Δε is obtained from equation (3).

Figure 19:
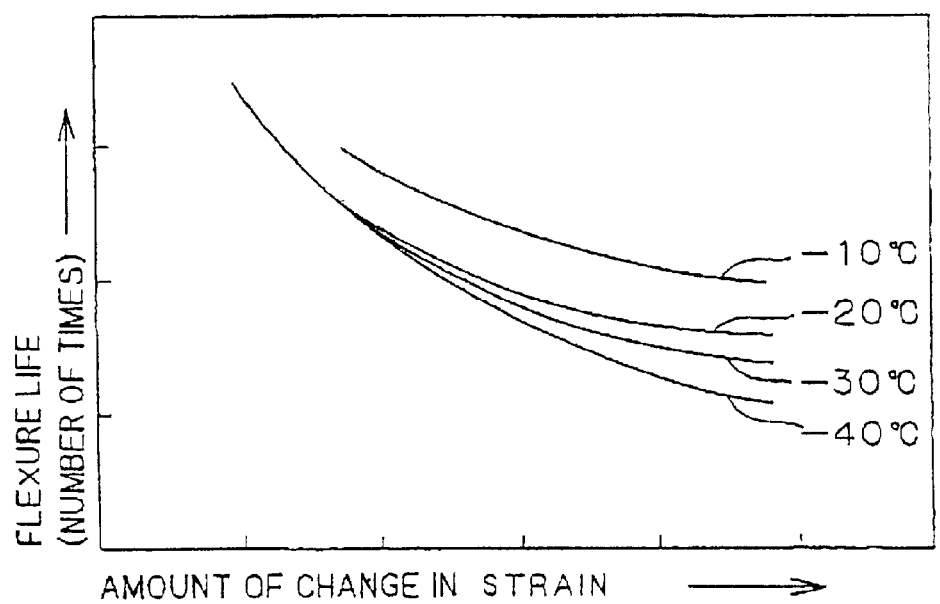
FIG. 19 is a drawing that shows a state in which master curves are obtained at respective temperatures.

Here, with respect to flexure life, the single wire is subjected to repeated bending, and it is found by actually measuring the number of bending processes up to disconnection. As described earlier, the disconnection of a wire bundle, etc., under low temperatures is mainly controlled by fatigue fracture of an insulating layer coating the conductor portion so that the flexure life has a temperature dependency. Therefore, with respect to measurements on the flexure life, measurements are carried out for each of required temperatures as shown in FIG. 19. The axis of abscissas represents the amount of change in strain, and the axis of ordinates represents the flexure life. As shown in FIG. 19, as the temperature decreases, the flexure property decreases, that is, the flexure life is shortened even at the same amount of change in strain.

2-2 Step of Calculating Amount of Change in Strain by Selecting Wires

Next, within wire bundle 1 to be subjected to measurements, with respect to the single wire that is assumed to have the greatest amount of change in strain Δε, the amount of change in strain Δε is calculated.

Figure 21:
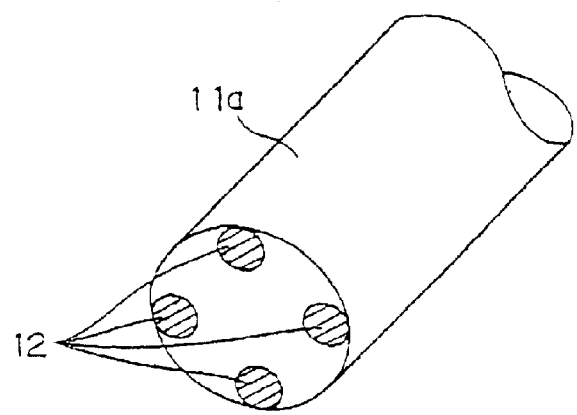
FIG. 21 is a drawing that shows a state in which the wire bundle is divided so as to analyze the amount of change in strain in accordance with the first preferred embodiment.

Here, at step S11 in FIG. 17, wire bundle 1 is not provided as a virtual single wire 11a that is obtained by transforming wire bundle 1 to a simple model, but determined so as to allow the shape of each wire 12 actually placed inside virtual single wire 11a to correspond to the shape of the above-mentioned virtual single wire 11, as shown in FIG. 21. In other words, based upon both of the shapes of virtual single wire 11 in the furthest bent state and in the furthest extended state outputted from step S08, by taking them into consideration the diameter Dx (see step S01A) of virtual single wire 11 and the dimension of the diameter of individual wires 12 ($d_y$ in equation (1)), both of the shapes of the wire 12 having the greatest amount of change in strain Δε inside thereof in the furthest bent state as well as in the furthest extended state are determined. In this case, as shown in FIG. 21, supposing that wire 12 is placed so as to contact the outer circumference of virtual single wire 11, a wire 12 having the greatest amount of change in strain Δε is selected among these as the wire 12 that is placed on the innermost circumferential side with respect to the bending radius of wire bundle 1. Here, in wire bundle 1, in some cases, a plurality of wires 12 are mutually placed in a twisted state, and in this case, it becomes difficult to predict which wire 12 comes to have the greatest amount of change in strain Δε; therefore, if there are a plurality of wires 12 having the greatest amount of change in strain Δε, the amount of change in strain Δε is calculated in each of the cases, and the wires 12 that are assumed to have the greatest amount of change in strain Δε are compared with each other so that the wire 12 may be selected after the comparison.

Then, after step S11, in the wire 12 that is assumed to have the greatest amount of change in strain Δε, the curvature radius R in the furthest extended state is set to $R_1$ while the curvature radius R in the furthest bent state is set to $R_2$, the amount of change in curvature ΔK is read from the curvature value file in accordance with the curvature value calculating process based upon the aforementioned finite element method of wire 12.

Next, at step S12, supposing that the radius of wire 12 is r, the amount of change in strain Δε is calculated in accordance with the above-mentioned equation (3) based upon the curvature value (value of curvature radius) of the selected wire 12:

Successively, at step S13, points of the selected wire 12 having the greatest amount of change in strain Δε found in step S12 are selected.

2-3 Collation Process to Master Curve (Life Estimation Curve)

Then, at step S14, the greatest amount of change in strain Δε, selected at step S13, is applied to the master curve (life estimation curve) shown in FIG. 19, and the value on the axis of ordinates at this time is obtained as an estimated value of the flexure life. Here, the correlation between the flexure life and the amount of strain of the selected wire 12 is not dependent on the radius of wire 12. Therefore, when the amount of change in strain of the selected wire 12 can be calculated through the curvature value calculation process based upon the aforementioned finite element method, it is possible to accurately estimate the flexure life independent of product conditions of the selected wire 12. Here, this fact does not necessarily mean that the method of estimation of flexure life of the selected wire 12 in accordance with the present invention is carried out without completely taking into consideration product conditions of the selected wire 12; and in a stage where the amount of change in strain of the wire 12 selected as an estimation subject is calculated in accordance with equation (3), the radius r is taken into consideration. With this arrangement, independent of product conditions of the selected wire 12, it is possible to accurately estimate the flexure life so that by reflecting the results of the estimation to designing of a wire harness, etc., it becomes possible to carry out desk-work examinations preliminarily, and consequently to provide optimal designing as well as to shorten the developing period. Moreover, it also becomes possible to reduce test devices that are actually used in estimations of flexure life.

Here, in the case when the stress of wire bundle 1 having a plurality of wires is analyzed based upon the finite element method, it is a rule that, originally, three dimensional analyses are carried out by using individual wires as discrete infinite elements; however, in the present preferred embodiment, the individual wires are not modeled three-dimensionally as discrete structural components, but dealt as a finite element by simplifying it into a virtual pseudo-single wire (virtual single wire 11), and after the shape has been determined by this step, the single wire 12 that is located at a position that provides the greatest amount of change in strain $\Delta\epsilon$ inside thereof is selected, and the estimation of flexure life is carried out only on this selected wire 12 in collation with the master curve. In this manner, in order to calculate the initial shape and the final shape, by carrying out modeling and calculations not based upon physical properties derived from the actual construction of wire bundle 1, but based upon the diameter Dx (see step S01) and bending elasticity of virtual single wire 11, it becomes possible to greatly simplify the physical properties of wire bundle 1 and also to calculate the resulting values. Consequently, it is possible to obtain an estimated value of flexure life that is closely-approximated to the actual flexure life. Therefore, upon calculating an estimated value of flexure life through finite element method (matrix stress analyzing method) by using a computer, it becomes possible to reduce the load imposed on the computer, and also to quickly converge the estimated value.

Moreover, in the above-mentioned curvature value calculation step, in the case when the shape of center line 8 of wire bundle to penetrate the inside of virtual pipe 9 is determined, calculations are carried out through finite element method as a completely free model (that is, a model in which the shape of center line 8 of wire bundle 1 does not have any influences from virtual pipe 9) with the existence of virtual pipe 9 being ignored; therefore, when a wire harness is applied as center line 8 of wire bundle 1, in comparison with a conventional case in which calculations are carried out on the assumption that it is secured to the center of the terminal of virtual pipe 9, it is possible to make the calculated value (estimated value) of flexure life closely approximate to the actual value of flexure life.

Figure 20:
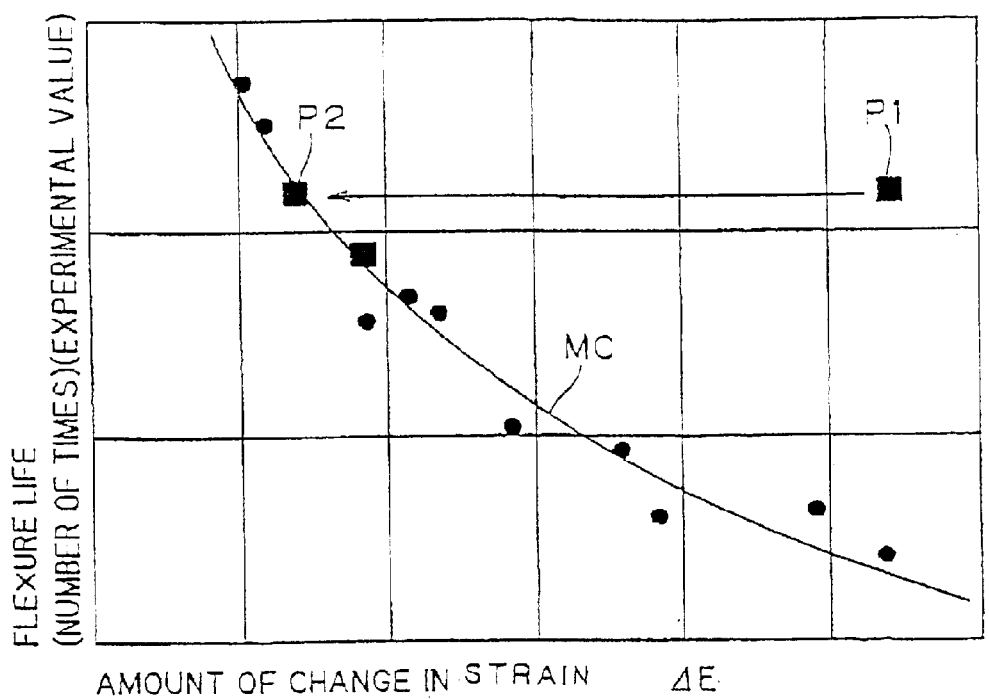
FIG. 20 is a drawing that shows a state in which amounts of change in strain, obtained based upon the curvature radius calculated in the curvature value calculation step, are fitted to the master curve in the estimated life outputting step.

More specifically, FIG. 20 shows an example in which a master curve (life estimation curve) MC is preliminarily set by using a predetermined single wire and the estimation of flexure life of wire bundle 1 is carried out by using the above-mentioned method of estimation of flexure life.

In the case when, without using the completely free model, the amount of change in strain $\Delta\epsilon$ is calculated on the assumption that center 8 of wire bundle 1 passes through the center of the terminal of virtual pipe 9 in a fixed manner, and when flexure life experiments are actually carried out and the number of extending and bending movements that have been taken up to disconnection is plotted, the results indicated by point P1 are obtained. However, it has been confirmed that this point P1 is plotted at a position greatly deviated from the master curve MC.

In contrast, in the case when the amount of change in strain $\Delta\epsilon$ is calculated by using the above-mentioned completely free model, and when flexure life experiments are actually carried out and the number of extending and bending movements that have been taken up to disconnection is plotted, the results indicated by point 2 are obtained. This point P2 is coincident with the master curve MC so that it has been proved that this preferred embodiment makes it possible to provide a method of estimation of flexure life with high precision.

Moreover, since it is possible to simplify the computer analyzing process by using a virtual pipe 9, the load of calculation processes on the computer can be greatly reduced. Moreover, since it is possible to eliminate the process of dividing virtual pipe 9 by using finite element meshes, it becomes possible to greatly reduce the work load.

Here, in the present embodiment, in steps S11 to S15, the life estimation is carried out on a single wire 12 having the greatest amount of change in strain $\Delta\epsilon$ in wire bundle 1 (virtual single wires 11a); however, instead of this arrangement, the estimation of flexure life may be simply carried out on the surface of virtual single wire 11 (see FIG. 16), and this may be used as the estimation of flexure life of wire 12. In this case, the diameter Dx of virtual single wire 11 (that is, the diameter of wire bundle 1: see step S01A) may be applied as the diameter r in equation (3) so as to carry out calculations.

{Preferred Embodiment 2}

The above-mentioned first preferred embodiment has discussed a method of estimating the flexure life that is applied to a case in which at low temperatures, cracks occur in the insulating layer serving as a coating portion prior to rupture of an inner conductor portion to cause a stress that is locally applied thereon, resulting in a disconnection in the inner conductive portion.

However, at normal temperature, in the case when a halogen-free resin material, PE, etc., that have very little temperature dependency are used as an insulating layer forming a coating material, or even in the case when an insulating layer such as PVC that has a temperature dependency is used, if these wire harnesses (wires or a wire bundle) are repeatedly bernt, a conductor portion, which forms an inner core line, sometimes has a disconnection prior to the occurrence of cracks due to fatigue fracture of the insulating layer. Therefore, at normal temperature, the disconnection of wire harnesses is not necessarily caused by fatigue fracture of the insulating layer coating the conductor portion, and it is considered that the flexure life of wire harness is equal to the flexure life of each strand inside thereof.

Moreover, for example, in an arrangement where a plurality of strands are placed inside a single insulating layer, when the respective flexure lives are compared between a strand placed in the center of the cross-section (hereinafter, referred to as "center conductor line") and strands placed on the periphery of this center conductor line, the peripheral strands, formed virtually in a coil shape, have a very long flexure life, while the center conductor line, which is linearly stretched, has a short flexure life. Moreover, in the case of a wire bundle in which a plurality of wires, each having a core line, are bundled, the flexure life of a core line (center conductor line) of any one of wires that has the greatest amount of change in strain between the furthest bent state and the furthest extended state is shortest. Here, it has been found that by estimating the life of only the center conductor line having the shortest flexure life, the flexure life of the entire wire harness can be estimated; in other words, it has been found that there is a strong correlation between the greatest amount of change in strain of only any one of the center conductor lines inside a wire harness and the flexure life of the wire harness as a whole.

In this case, with respect to the master curve, a master curve is preliminarily found from a wire having the same materials in the conductor portion (for example, copper) and the coating material, and with respect to the conductor portion (center conductor line) of the wire 12 having the greatest amount of change in strain $\Delta\epsilon$ in wire bundle 1, the amount of change in strain $\Delta\epsilon$ is found based upon finite element method, and the estimation of flexure life of the conductor portion may be carried out by collating the results with the master curve. In this manner, by preliminarily finding the correlation between the amount of change in strain of the center conductor line and the flexure life of the center conductor line, it becomes possible to estimate the flexure life of a wire harnesse as a whole by only analyzing the greatest amount of change in strain with respect to the center conductor line under various product conditions. The method of estimation of flexure life in accordance with the present preferred embodiment has been devised based upon the above-mentioned knowledge.

Here, as will be described below, in the present method of estimating the flexure life of wire harnesses, in a structure having a plurality of conductor lines (strands or core lines), by estimating the flexure life of any one of center conductor lines that is assumed to have the shortest flexure life, the flexure life of the wire harness (wire of wire bundle) as a whole is estimated; however, with respect to a subject such as a wire bundle with a structure having a plurality of conductor lines, the flexure life in the present preferred embodiment does not necessarily estimate complete disconnection of all the conductor lines in the wire or wire bundle. Even when any one of conductor lines (including the center conductor line) within a wire or a wire bundle has a disconnection, the other conductor lines are not necessarily disconnected at the same time, and the complete disconnection of all the wires in the wire or the wire bundle occurs after a lapse of considerable time. However, since the fact that any one of conductor lines (that is, the center conductor line having the shortest flexure life) is disconnected means a great change in the functional quality of the wire or the wire bundle, the present preferred embodiment defines the life up to disconnection of any one of conductor lines as the flexure life although this does not cause complete disconnection.

Among specific methods of estimation of flexure life, the following description will discuss a method of estimating the flexure life for a wire (see FIG. 25) formed by twisting strands 102 on the periphery of a center conductor line 101 as a second preferred embodiment.

Figure 22:
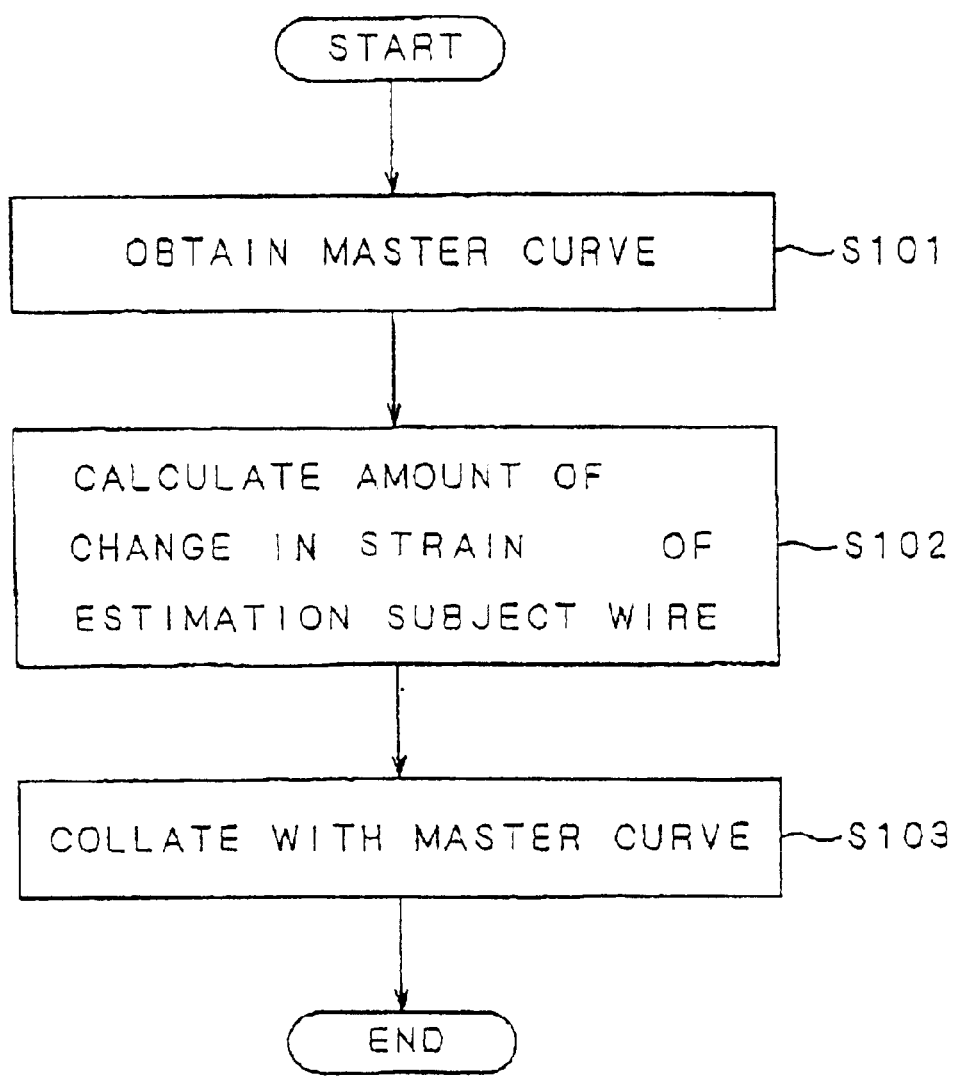
FIG. 22 is a flow chart that shows a flow chart that shows a wire harness flexure life estimating method in accordance with a second preferred embodiment of the present invention.

FIG. 22 is a flow chart that shows a sequence of this method of estimating the flexure life (the outline of a basic flow is the same as the first preferred embodiment).

Figure 23:
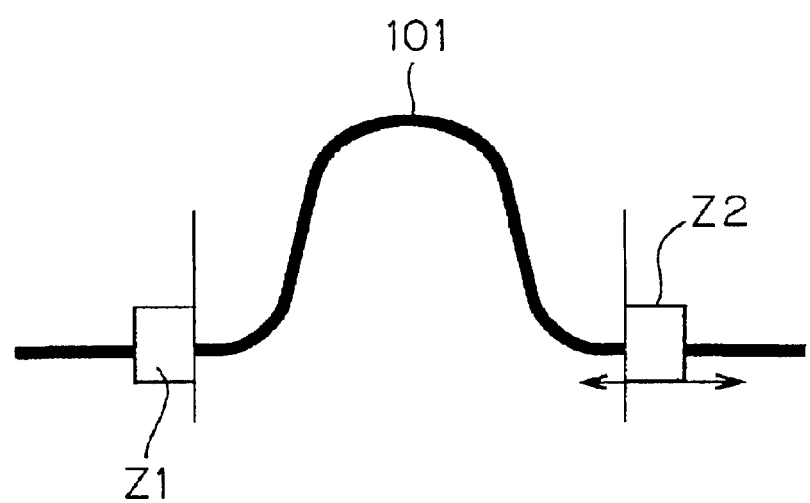
FIG. 23 is a drawing that shows a bending test of a single wire that is carried out so as to obtain a master curve.

First, at step S101 that is a pre-step, a master curve indicating a correlation between the flexure life and the amount of change in strain of a single wire is preliminarily obtained. With respect to the master curve, a strand 101, which is, for example, a single product of copper made of the same material as the center conductor line to be actually used, is subjected to repeated bending processes by using predetermined tools Z1, Z2 as shown in FIG. 23 (in an example shown in FIG. 23, the tool Z2 is reciprocally moved in the direction of arrow with respect to the tool Z1), and the amount of change in strain is analyzed by using CAE analysis, etc., and the flexure life (the number of bending processes up to disconnection) is actually measured with respect to various amounts of change in strain; thus, the master curve is obtained.

Figure 16:
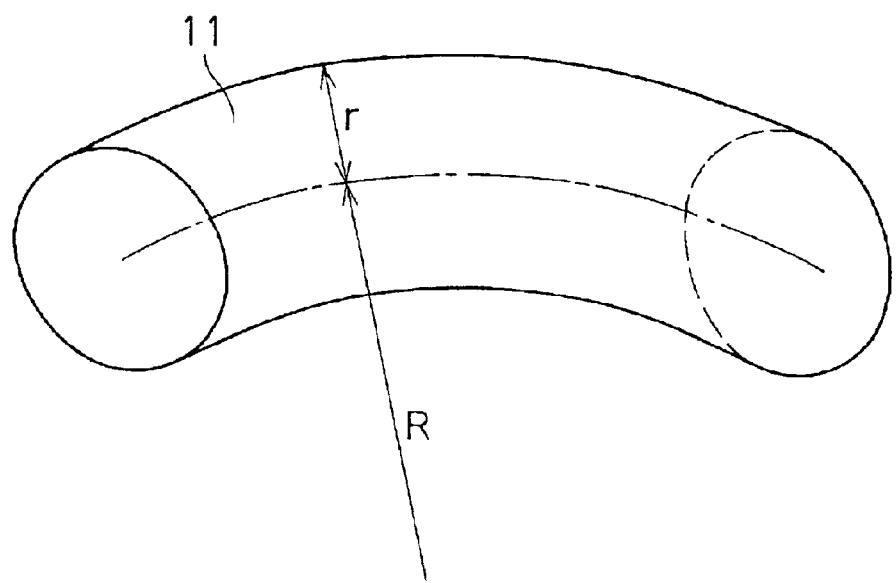
FIG. 16 is a drawing that explains an amount of change in strain of a wire.

Then, as shown in FIG. 16, the radius of conductor line (single wire) 101 inside the insulating layer in a wire (indicated by reference numeral 11 in FIG. 16) is defined as r. The conductor line 101 is subjected to a bending deformation, and supposing that the bending radius is R, the curvature K is represented by K=1/R. At this time, strain $\epsilon$ appearing on the surface of conductor line 101 is represented by the above-mentioned equation (2) (the first preferred embodiment).

Here, in conductor line 101 placed at a position that is subjected to bending from the door portion and sheet portion, supposing that the bending radius is $R_1$ in conductor line 101 in the furthest bent state at the position that is subjected to the bending, that the bending radius is $R_2$ in conductor line 101 in the furthest extended state, and that the amount of change in strain on the surface of the corresponding conductor line 101 is $\Delta\epsilon$, when conductor line 101 is repeatedly extended and bent between the furthest extended state and the furthest bent state, $\Delta\epsilon$ is represented by the above-mentioned equation (3) (the first preferred embodiment).

Here, in equation (3), $\Delta K$ represents the amount of change in curvature when conductor line 101 is subjected to repeated bending, and in the same manner as the first preferred embodiment, this value is calculated through a computer analysis (so-called CAE analysis) based upon finite element method from the change in shape of conductor line 101 at the time of the repeated bending. The calculated value $\Delta K$ is listed with respect to each portion of conductor line 101, and $\Delta K$ having the greatest value is adopted so that the greatest amount of change in strain $\Delta\epsilon$ on the surface of conductor line 101 is obtained from equation (3).

Here, with respect to flexure life, conductor line 101 is subjected to repeated bending, and it is found by actually measuring the number of bending processes up to disconnection. Disconnection of the wire harness as a whole at normal temperature is mainly dependent on the metal fatigue fracture of each conductor line 101 inside thereof; however, in the case when there is a temperature dependence in flexure life, it is preferable to carry out the measurements of flexure life for each range of required temperatures.

Here, with respect to conductor line 101 used for determining a master curve, it is necessary to use one that uses the same materials as the conductor line and insulating material that are used in the wire harness that is an actual estimation subject; however, with respect to the diameter thereof, this is not necessarily set to the same as that of a wire harness that is the estimation subject. This is because the inventors, etc. of the present invention have obtained through experiments the knowledge that even when master curves have been preliminarily found by using samples having different diameters in conductor line, the corresponding master curve can be applied independent of the radius of conductor line 101 serving as the subject of the estimation.

Figure 24:
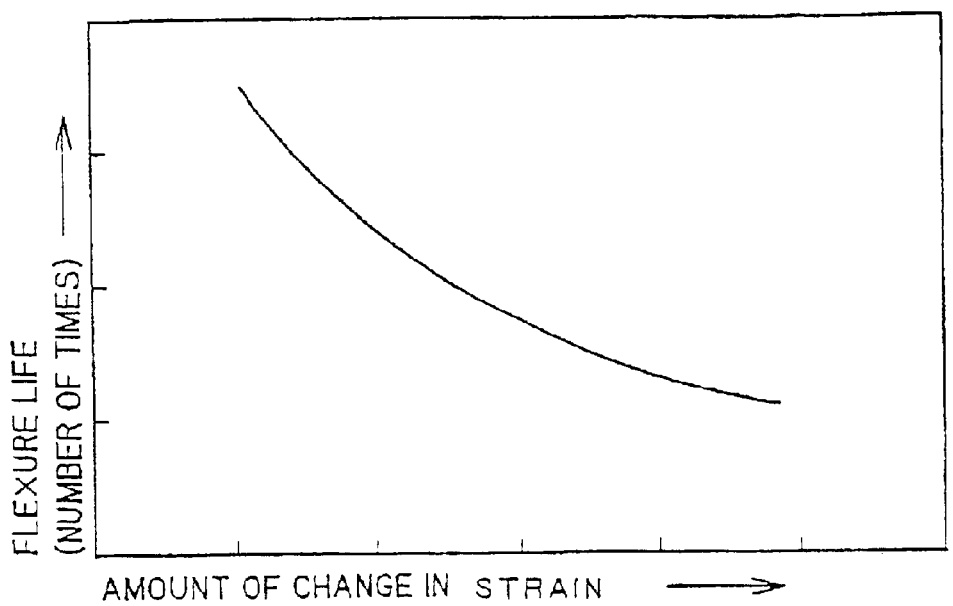
FIG. 24 is a drawing that shows a master curve.

FIG. 24 is a drawing that shows one example of a master curve thus obtained. The axis of abscissas in this Figure represents the amount of change in strain of the surface of conductor line 101, and the axis of ordinates represents the flexure life (the number of bending processes up to disconnection).

Now, in FIG. 22 again, after acquiring a master curve, the sequence proceeds to step S102 where the greatest amount of change in strain $\Delta\epsilon$ of the center conductor line of a wire harness that is a subject for the estimation of flexure life is calculated. The greatest amount of change in strain $\Delta\epsilon$ of the center conductor line of the wire harness that is a subject for the estimation of flexure life is calculated through shape simulations using a computer, and based upon the attached state of the wire harness, the attached shape and the states of bending strain received after the attaching process, calculations are executed through a CAE analysis based upon finite element method. Here, the greatest amount of change in strain $\Delta\epsilon$ of the center conductor line to be calculated here is found in the same processes as those used when the master curve is obtained.

More specifically, the greatest amount of change in strain $\Delta\epsilon$ of the center conductor line of the wire harness that is a subject for the estimation of flexure life is obtained as follows: for example, first, the initial shape of a wire harness is virtually reproduced in a computer as a finite element model, the bending and extending states of the actual wire harness are simulated together with the movements (for example, door opening and closing movements, etc.) of a place to which it is attached, and with respect to a point having the greatest change in the curvature radius ($1/R_1-1/R_2$) with respect to the center conductor line, the greatest amount of change in strain $\Delta\epsilon$ at this portion is found based upon the above-mentioned equation (3). Here, in such a computer analyzing process based upon finite element method, it is essential to reproduce the actual state of a wire harness in the finite element model; therefore, the bending radius (curvature radius) R needs to be considered by taking into consideration various physical properties such as the thickness of an insulating layer forming a coating material and bending elasticity.

For example, the bending modulus of elasticity of a metal material of a conductor portion and the bending modulus of elasticity of an insulating material of a coating layer are subjected to weighting processes and averaged based upon the ratio of cross-sectional areas thereof, and a virtual material, which is obtained by averaging the metal material of the conductor portion and the insulating material of the coating layer, is assumed. Then, such a virtual material is formed into a line material (hereinafter, referred to as "virtual line member"), and the shape thereof is determined by assuming the radius and the bending radius of the virtual line member.

Figure 25:
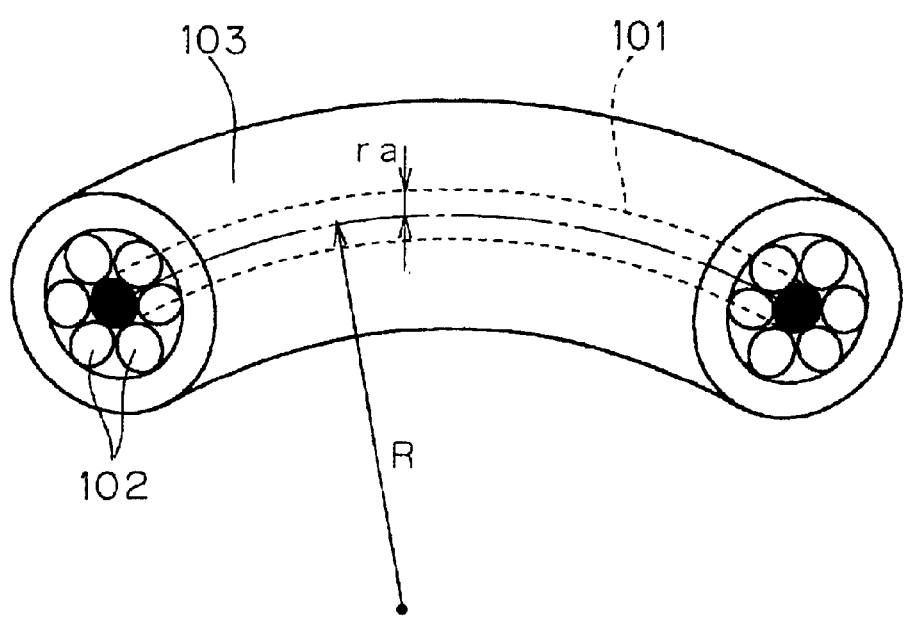
FIG. 25 is a drawing that shows a state in which a center conductor line is contained in a wire.

After such a process, in the present preferred embodiment, as illustrated in FIG. 16 (in the same manner as the first preferred embodiment), the curvature radius R (that is, $R_1$, $R_2$ in equation (3)) is found with respect to only center conductor line 101 (indicated by reference number 11 in FIG. 16) of the wire harness so that the greatest amount of change in strain $\Delta\epsilon$ is obtained. In this manner, as shown in FIG. 25, in the case of a wire which is formed by twisting strands 102 on the periphery of center conductor line 101, the respective curvature radii ($R_1$, $R_2$) in extending and bending movements are found by taking into consideration only the single center conductor line 101 inside thereof.

Then, by taking $R_1$ (bending radius of the virtual line member in the furthest bent state) and $R_2$ (bending radius of the virtual line member in the furthest extended state) shown equation (3) into consideration, the greatest amount of change in strain ($\Delta\epsilon$ in equation (3)) of center conductor line 101 is calculated.

Next, by collating the greatest amount of change in strain of conductor line 101 serving as a subject for estimation, thus calculated, with the above-mentioned master curve (FIG. 24), the flexure life of the wire harness as a whole is estimated (step S103). As has been described, the correlation between the flexure life of a wire harness and the greatest amount of change in strain of its center conductor line 101 is not dependent on the shapes of the wire harness and center conductor line 101. Therefore, by calculating the greatest amount of change in strain of center conductor line 101, it becomes possible to correctly estimate its flexure life, independent of the radius of the wire. Here, this fact does not necessarily mean that the method of estimating the flexure life of a wire in accordance with the present invention is carried out without taking into consideration the radius of the wire; and in a stage where the amount of change in strain of the wire serving as an estimation subject is calculated in accordance with equation (3), the radius thereof is taken into consideration.

With this arrangement, independent of product conditions of a wire, it is possible to accurately estimate the flexure life so that by reflecting the results of the estimation to designing of a wire harness, etc., it becomes possible to carry out desk-work examinations preliminarily, and consequently to provide optimal designing as well as to shorten the developing period.

Figure 26:
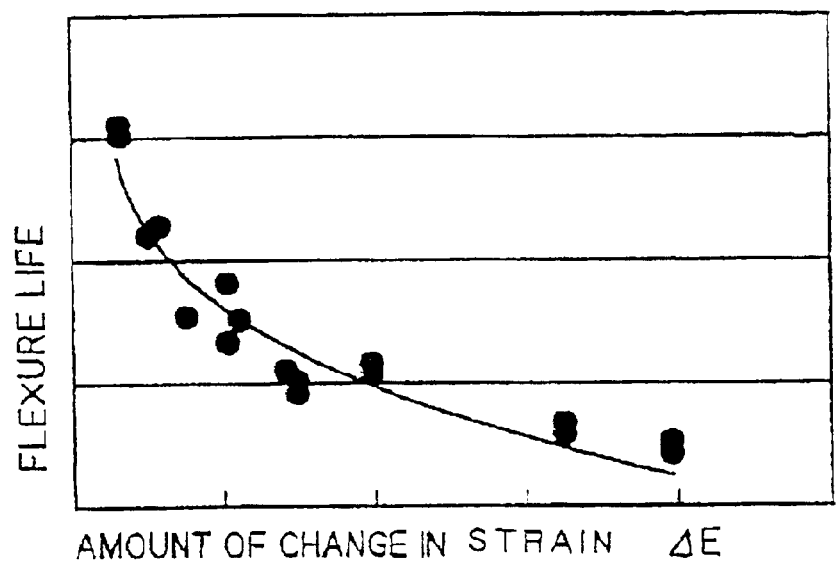
FIG. 26 is a drawing that shows a state in which data as the results of tests are plotted on the master curve.

FIG. 26 is a drawing that compares the results of the experiment with the master curve. Here, the experiments are carried out on various wires having conductor portions (core lines) having various diameters. As shown in FIG. 26, the correlation between the greatest amount of change in strain of the center conductor line and the flexure life is formed by plotted dots shown in FIG. 26; as a result, it is confirmed that the life of the actual wire harness is virtually coincident with the master curve obtained based upon the bending tests using a signal line, independent of the diameters of the conductor portion.

{Third Preferred Embodiment}

Figure 27:
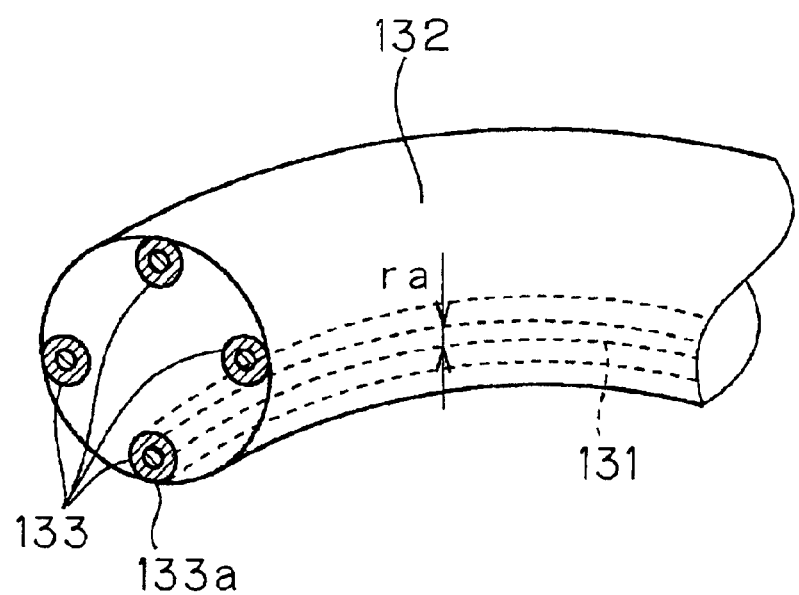
FIG. 27 is a drawing that shows a bent state of the wire bundle.

In the above-mentioned second embodiment, as shown in FIG. 25, the explanation has been given of the method of estimation of flexure life with respect to a wire formed by aligning center conductor line 101 in the center of strands 102; and in a third preferred embodiment, as shown in FIG. 27, an explanation will be given of a method of estimation of flexure life with respect to a wire bundle 132 formed by bundling a plurality of wires 133, each having a core line (center conductor line) 131. Here, since the method of estimation of flexure life in accordance with the present preferred embodiment is the same as the second preferred embodiment in its most portions, the explanation is given centered on portions different from the second preferred embodiment.

First, in the case of a wire bundle 132 serving as a subject of the estimation of flexure life, a plurality of wires 133 are placed in parallel with each other, and in the case when these wires 133 are collectively bent as wire bundle 132, one of the wires 133a located at the innermost position in the bending radius has the greatest change in curvature radius (1/R1−1/R2). Therefore, by selecting only the center conductor line 131 of this single wire 133*a* having the greatest change in curvature radius as a subject for the estimation of flexure life, it becomes possible to easily carry out the estimation of flexure life.

First, with respect to the acquiring process of a master curve at step S101, the completely same method as the second preferred embodiment is carried out.

Next, at step S102, in the case when the subject for the estimation of flexure life is wire bundle 132 shown in FIG. 27, the respective core lines of all the wires 133 and bending modulus of the insulating layer are subjected to weighting processes and averaged based upon the respective ratios of cross-sectional areas so that a virtual material in which the metal material of the conductor portion and the insulating material of the insulating layer are comprehensively averaged is assumed so that the shape (bent shape and extended shape) of wire bundle 132 as a whole is determined.

In the shape of wire bundle 132 thus determined as a whole, with respect to a single wire 133*a* that is located on the innermost side of the curvature radius and that is expected to have the greatest change in its curvature radius among the core lines in wires 133 inside wire bundle 132, the change of the curvature radius R (that is, $R_1$ and $R_2$ in equation (3)) of only the center conductor line 131 of wire 133*a* is found.

Then, this curvature radius R (that is, $R_1$ and $R_2$ in equation (3)) is substituted into equation (3) with the radius of center conductor line 131 of the corresponding wire 133 being set to r, so that the greatest amount of change in strain $\Delta\epsilon$ on the surface of center conductor line 131 is calculated.

At step S103, the greatest amount of change in strain $\Delta\epsilon$ is applied to the master curve, thereby estimating the flexure life of the wire harness as a whole.

Here, in the case when wires 133 inside wire bundle 132 are mutually twisted and placed, in some cases, it is not possible to predict which wire 133 has the greatest change in the curvature radius. In such a case, the estimation of flexure life is carried out on each of wires 133, and the flexure life of the wire 133 that has been estimated to have the shortest flexure life is determined as a flexure life of wire bundle 132 as a whole.

As described above, in the present preferred embodiment, assuming a virtual single wire 11 prepared by modeling wire bundle 1 into a single wire, and after the shape of virtual single wire 11 has been determined in the same manner as steps S01 to S08 in the above-mentioned first preferred embodiment, any one of wires 12 that makes the amount of change in strain $\Delta\epsilon$ greatest is selected, and after the shape of the conductor portion inside thereof has been determined based upon the shape of virtual single wire 11, the estimation of flexure life is then carried out on only the corresponding conductor portion. In this case, the diameter of the conductor portion is applied as diameter r in equation (3).

With this arrangement, not only with respect to the flexure life of wire bundle 1 under the low temperature environment but also with respect to the flexure life of wire bundle 1 under the normal temperature environment, the estimation of flexure life of wire bundle 132 is easily carried out, making it possible to reduce the load imposed on the computer and also to predict the flexure life correctly.

{Fourth Preferred Embodiment}

The above first preferred embodiment has exemplified a case in which, when wire bundle 1 is allowed to penetrate the inside of grommet 2 placed in the vicinity of a hinge portion and when wire bundle 1 is extended and bent in response to the opening and closing operations of door 3, the flexure life of wire bundle 1 is estimated; however, the above-mentioned basic method is also applied to a case in which external attachments such as grommets are not taken into consideration.

Figure 28:
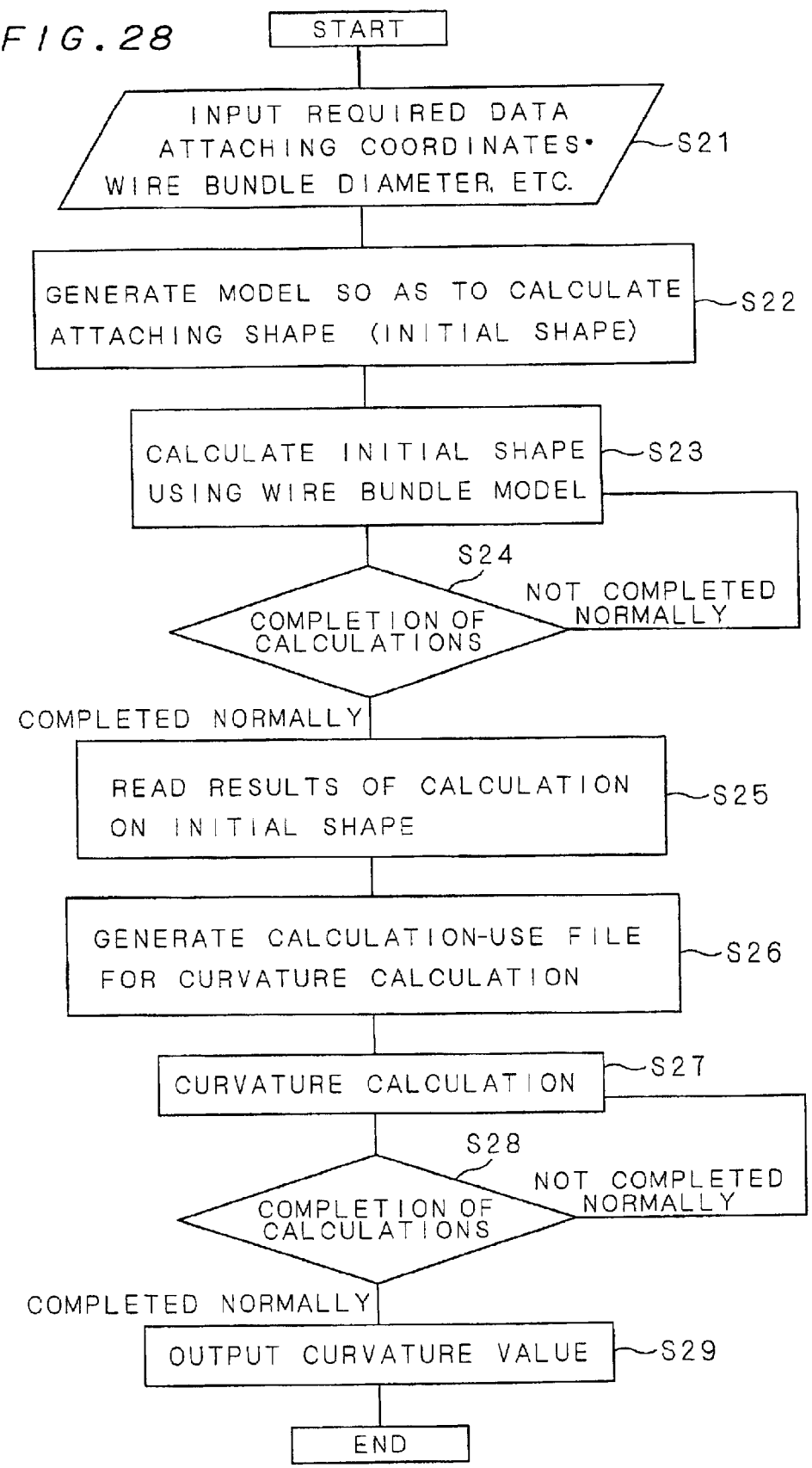
FIG. 28 is a flow chart that shows a curvature value calculation step in a flexure life estimating step in accordance with a fourth preferred embodiment.

In this case, as shown in step S21 in FIG. 28 (corresponding to step S01 in FIG. 3), first, various kinds of parameters, such as an attaching position (clamp position) of a wire harness (in this case, wire bundle), a dimension of the wire harness (the diameter and length of the wire bundle) and the movement direction and the amount of movement of the terminal point of the wire bundle, are inputted. By inputting these parameters, a procedure file for forming an analyzing model is formed. This procedure file includes not only parameters, but also all the various command lines on programs for forming a three-dimensional shape. Material physical properties of the wire harness are included in this procedure file so that the procedure file is allowed to include all the values of the respective parameters.

Next, at step S22, the procedure file, formed at step S21, is executed. In this manner, the procedure file is executed on a predetermined three-dimensional shape forming application program so that the initial shape model of the wire bundle (three-dimensional shape model) is automatically formed on the three-dimensional shape forming application program. Then, at step S23, with respect to the initial shape of the wire bundle, the attaching position and attaching shape are calculated.

At the next step S24, it is determined whether or not the calculations are normally completed. If it is not completed normally, a check is made for the abnormal completion, and the procedure file (parameters and command lines) for a model to be calculated is revised by using an editor and an exclusively-used software program; then, procedures from step S21 to S24 are executed repeatedly.

Thereafter, the sequence proceeds to step S25 where the calculation results of the initial shape are read so as to form a calculation-use file for curvature calculations (step S26).

This calculation-use file (door opening and closing model and contact definition) formed at step S26 is used for calculating the curvature at the time of opening and closing the door at step S27. With respect to numeric values to be outputted at this time, the curvature at each joint in the center position of the wire bundle. Such a numeric value (curvature) is temporarily stored in a file, and then used for calculating the amount of change in strain (as described earlier) at the post-process. Here, if the calculations are not completed normally, re-calculations are repeated by revising conditions of the calculations (for example, the number of steps, etc.)(step S28).

Then, at step S29, the curvature of each joint calculated at step S27 and the value of the curvature at each step are stored as a curvature file. With respect to these values of curvature, the value at the center position of the wire bundle is adopted. Based upon this curvature file, the amount of change in strain used for estimating the life of the wire bundle is calculated in the same manner as the first preferred embodiment based upon this curvature file.

With respect to the method for estimating the life based upon the curvature value, the same sequence as that explained in FIG. 17 is carried out. Among the values of the life obtained here, the value corresponding to the shortest life is retrieved, and this forms the estimated flexure life of the wire harness.

In this manner, even in the case when no external attachments are taken into consideration, the shape of the wire harness (in this case, wire bundle) when it is bent is calculated by using the CAE method, and based upon the value of strain of the wire bundle thus obtained, the amount of change in strain is calculated, and based upon this value, it is possible to easily calculate the flexure life of the wire harness. Therefore, the number of bending processes up to disconnection of the wire harness is calculated by the CAE method, making it possible to easily predict the life of the wire harness on a software basis. Therefore, it becomes possible to reduce corresponding evaluation tests.

Moreover, as described in the preferred embodiments, by preliminarily defining various parameters and command lines with respect to various models by using a procedure file, the revision of the parameters in the course of the procedure is easily carried out. Moreover, many procedure files may be preliminarily prepared, and based upon these, the estimation of the life is carried out, thereby making it possible to provide a more convenient method.

While the present invention has been described in detail, the foregoing description is in all aspects illustrative and not restrictive. It is understood that numerous other modifications and variations can be devised without departing from the scope of the present invention.

While the invention has been shown and described in detail, the foregoing description is in all aspects illustrative and not restrictive. It is therefore understood that numerous modifications and variations can be devised without departing from the scope of the invention.

The present disclosure relates to subject matter contained in priority Japanese Patent Application Nos. 2001-058445, filed on Mar. 2, 2001, 2001-057945, filed on Mar. 2, 2001, and 2001-341614, filed on Nov. 7, 2001, the contents of all of which are herein expressly incorporated by reference in their entireties.

What is claimed is:

1. A method of estimating flexure life of a wire harness in which, in the case when a wire bundle, formed by binding a plurality of wires each formed by coating a conductor line with an insulating layer, is allowed to pass through a predetermined protective tube and secured to an external structural member different from said protective tube, the flexure life up to disconnection caused by extending and bending processes of said wire bundle caused by operations of said external structural member is estimated in accordance with a finite element method, comprising:

an initial shape determining step of:
using an initial shape of a center line of said wire bundle as a substitute for an initial shape of said wire bundle so as to be determined, using an initial shape of a virtual pipe having only a margin dimension of a margin space of said protective tube with respect to said wire bundle as an inner diameter as a substitute for an initial shape of said protective tube so as to be determined, determining an initial shape of a center line of said wire bundle so that the center line of said wire bundle is not limited by two end portions of the virtual pipe, and determining an initial shape of said external structural member;

an extending and bending operation analyzing step of:
analyzing extending and bending shapes of said wire bundle and said protective tube by virtually estimating operations of said external structural member so as to calculate a change in curvature of said wire bundle; step; and a collation step of: making a collation on a life estimation curve that is preliminarily set based upon said amount of change in strain calculated in said calculation step of an amount of change in strain so as to predict the flexure life of said wire bundle.

2. The method of estimating flexure life of a wire harness according to claim 1, wherein, in said extending and bending operation analyzing step, a change in curvature of a center line of the wire bundle is used as a substitute for said change in curvature of the wire bundle.

3. The method of estimating flexure life of a wire harness according to claim 1 wherein: said life estimation curve represents correlation between the amount of change in strain and said number of bending processes with respect to a single wire that is obtained by actually measuring the number of bending processes up to disconnection by repeatedly bending said single wire with respect to a plurality of amounts of change in strain; and in said calculation step of an amount of change in strain, a virtual line member, formed by subjecting the respective bending modulus of elasticity of said conductor line and said insulating layer to weighting processes and averaging processes by using ratios of cross-sectional areas, is assumed, and on the assumption that the virtual line member serves as one of said wires, supposing that the bending radius is $R_1$ in any one of the wires in the furthest bent state at the position that is subjected to the greatest change in bending within an area in which said virtual line member is subjected to bending, that the bending radius is $R_2$ in the single wire in the furthest extended state, and that the radius of any one of wires that has the greatest difference between said value $R_1$ and said value $R_2$ is r, said amount of change in strain ($\Delta\epsilon$) is calculated by the following equation:

$$\Delta\epsilon = r \cdot (1/R_1 - 1/R_2)$$

4. A method of estimating flexure life of a wire harness, which includes a wire having at least a center conductor line in the center thereof with strands twisted on the periphery of the center conductor line, and has a function for estimating flexure life up to disconnection of said wire due to bending and extending processes, comprising the steps of:

preliminarily obtaining a correlation between an amount of change in strain of a single wire that is made of the same material as said center conductor line and actual measured values of flexure life;

calculating the greatest amount of change in strain of said center conductor line of a wire serving as a subject for the estimation; and estimating flexure life of said wire by collating said calculated greatest amount of change in strain of said center conductor line with said correlation.

5. The method of estimating flexure life of a wire harness according to claim 4, wherein, in said step of obtaining the correlation, said single wire is repeatedly bent with respect to a plurality of amounts of change in strain to actually measure the number of bending processes up to disconnection so as to obtain the correlation.

6. The method of estimating flexure life of a wire harness according to claim 4, wherein, said calculation step of the greatest amount of change in strain, supposing that the center conductor line has a radius of r, that the bending radius is $R_1$ in said center conductor line in the furthest bent state at the position that is subjected to the greatest change in bending within an area in which said center conductor line is subjected to bending, and that the bending radius is $R_2$ in said center conductor line in the furthest extended state, said greatest amount of change in strain ($\Delta\epsilon$) is calculated by the following equation:

$$\Delta\epsilon = r \cdot (1/R_1 - 1/R_2).$$

7. A method of estimating flexure life of a wire harness, which includes a wire bundle formed by binding a plurality of wires, each having a central conductor line in the center thereof, and has a function for estimating flexure life up to disconnection of said wire bundle, comprising the steps of:

preliminarily obtaining a correlation between an amount of change in strain of a single wire that is made of the same material as said center conductor line and actual measured values of flexure life;

calculating the greatest amount of change in strain of said center conductor line of a single wire that is assumed to have the greatest change in curvature radius upon being bent among the wires within the wire bundle serving as a subject for the estimation; and estimating flexure life of said wire bundle by collating said calculated greatest amount of change in strain of said center conductor line of said wire with said correlation.

8. A wire harness designing method, which is used for designing a wire harness in which a single or a plurality of wires, each formed by coating a conductor line with an insulating layer, are bound and placed on a desired application subject, comprising:

an application subject design planning step of planning a design of said application subject as a whole;

a wire harness design planning step of planning a design of said wire harness so as to fit to said application subject; and a flexure life estimating step of estimating flexure life of said wire harness planned at said wire harness design planning step up to disconnection caused by extending and bending processes of said wire harness in accordance with a finite element method, said flexure life estimating step comprising:

an initial shape determining step of determining an initial shape of said wire harness;

an extending and bending operation analyzing step of: analyzing extending and bending shapes of said wire harness so as to calculate a change in curvature of said wire harness;

a calculation step of an amount of change in strain for calculating an amount of change in strain of said wire harness that is a subject for estimation based upon the change in curvature obtained through said extending and bending operation analyzing step; and a collation step of: making a collation on a life estimation curve that is preliminarily set based upon said amount of change in strain calculated in said calculation step of an amount of change in strain so as to predict the flexure life of said wire harness.

9. A wire harness designing method, which is used for designing a wire harness in which a single or a plurality of wires, each formed by coating a conductor line with an insulating layer, are bound and placed on a desired application subject, comprising:

an application subject design planning step of planning a design of said application subject as a whole;

a wire harness design planning step of planning a design of said wire harness so as to fit to said application subject; and a flexure life estimating step of, in the case when said wire harness planned in said wire harness design planning step is allowed to pass through a predetermined protective tube and secured to an external structural member different from said protective tube, estimating flexure life up to disconnection caused by extending and bending processes of said wire harness in accordance with a finite element method, said flexure life estimating step comprising:

an initial shape determining step of: using an initial shape of a center line of said wire harness as a substitute for an initial shape of said wire harness so as to be determined, using an initial shape of a virtual pipe having only a margin dimension of a margin space of said protective tube with respect to said wire harness as an inner diameter as a substitute for an initial shape of said protective tube so as to be determined, determining an initial shape of a center line of said wire harness so that the center line of said wire harness is not limited by two end portions of the virtual pipe, and determining an initial shape of said external structural member;

an extending and bending operation analyzing step of: analyzing extending and bending shapes of said wire harness and said protective tube by virtually estimating operations of said external structural member so as to calculate a change in curvature of said wire harness;

a calculation step of an amount of change in strain for calculating an amount of change in strain of said wire harness that is a subject for estimation based upon the change in curvature obtained through said extending and bending operation analyzing step; and a collation step of: making a collation on a life estimation curve that is preliminarily set based upon said amount of change in strain calculated in said calculation step of an amount of change in strain so as to predict the flexure life of said wire harness.

10. The wire harness designing method according to claim 9, wherein: said application subject design planning step and said wire harness design planning step are executed by an application subject designing station for designing and planning said application subject, and said flexure life estimating step is executed by a wire manufacturing station for manufacturing said wire harness or said application subject designing station.

11. The wire harness designing method according to claim 9, wherein in said extending and bending operation analyzing step in said flexure life estimating step, said change in curvature of the center line of said wire bundle is used as a substitute for said change in curvature of the wire bundle.

12. The wire harness designing method according to claim 9, wherein: in said flexure life estimating step, said life estimation curve represents correlation between the amount of change in strain and said number of bending processes with respect to a single wire that is obtained by actually measuring the number of bending processes up to disconnection by repeatedly bending said single wire with respect to a plurality of amounts of change in strain; and in said calculation step of an amount of change in strain in said flexure life estimating step, a virtual line member, formed by subjecting the respective bending modulus of elasticity of said conductor line and said insulating layer to weighting processes and averaging processes by using ratios of cross-sectional areas, is assumed, and on the assumption that the virtual line member serves as one of said wires, supposing that the bending radius is $R_1$ in any one of the wires in the furthest bent state at the position that is subjected to the greatest change in bending within an area in which said virtual line member is subjected to bending, that the bending radius is $R_2$ in the single wire in the furthest extended state, and that the radius of any one of wires that has the greatest difference between said value $R_1$ and said value $R_2$ is r, said amount of change in strain ($\Delta\epsilon$) is calculated by the following equation:

$\Delta\epsilon = r \cdot (1/R_1 - 1/R_2)$.

13. The wire harness designing method according to claim 9, wherein in said initial shape determining step of said flexure life estimating step, the initial shape of said wire harness is determined based upon at least the diameter of said wire harness, the diameter of said wire harness being calculated through a predetermined arithmetic expression based upon the number and diameters of a plurality of kinds of wires constituting the wire harness.

14. The wire harness designing method according to claim 9, wherein in said initial shape determining step of said flexure life estimating step, said margin dimension is found by subtracting the diameter of said wire harness from the inner diameter of said protective tube, the diameter of said wire harness being calculated through a predetermined arithmetic expression based upon the number and diameters of a plurality of kinds of wires constituting the wire harness.

15. The wire harness designing method according to claim 14, wherein supposing that the respective wires constituting said wire harness have a diameter of $d_v$, that the number of the respective wires having the diameter $d_v$, is $N_v$, and that a predetermined coefficient is $a_1$, the diameter $D_x$, of said wire harness is calculated by the following equation:

$$D_0 = \left\{ \sum_{v=1}^{m} (d_v^2 \times N_v) \right\}^{1/2} \quad \text{[Equation 2]}$$

$$Dx = \sum_{i=1}^{n} (a_i \times D_0^1).$$

16. The program for allowing a computer to execute the respective steps within the flexure life estimating step in order to realize said flexure life estimating step on the computer in a wire harness designing method disclosed in claim 9.

* * * * *